(12) United States Patent
Litvin

(10) Patent No.: US 7,400,927 B1
(45) Date of Patent: Jul. 15, 2008

(54) METHOD AND SYSTEM FOR PSYCHOLOGICAL TREATMENT BY BRAIN STIMULATION OF THE PSYCHOLOGICALLY DISORDERED OBJECT

(76) Inventor: Chester Litvin, 6229 Morse Ave., North Hollywood, CA (US) 91606

( * ) Notice: Subject to any disclaimer, the term of this patent is extended or adjusted under 35 U.S.C. 154(b) by 169 days.

(21) Appl. No.: 11/030,689

(22) Filed: Jan. 6, 2005

(51) Int. Cl.
*A61N 1/00* (2006.01)

(52) U.S. Cl. .......................................... 607/45; 128/898
(58) Field of Classification Search ................... 607/45; 600/558, 559; 128/898; 434/433
See application file for complete search history.

(56) References Cited

U.S. PATENT DOCUMENTS

| | | | |
|---|---|---|---|
| 6,167,311 A | 12/2000 | Rezai | |
| 6,418,344 B1 | 7/2002 | Rezai et al. | |
| 6,425,764 B1 * | 7/2002 | Lamson | 434/236 |
| 6,443,977 B1 | 9/2002 | Jaillet | |
| 6,520,905 B1 | 2/2003 | Surve et al. | |
| 6,556,868 B2 | 4/2003 | Naritoku et al. | |
| 6,708,064 B2 | 3/2004 | Rezai | |
| 6,798,898 B1 | 9/2004 | Fedorovskaya et al. | |

* cited by examiner

*Primary Examiner*—Carl H. Layno
*Assistant Examiner*—Eric D Bertram

(57) ABSTRACT

The method and system for psychological treatment by brain stimulation of the psychologically disordered object provide a possibility to stimulate the simple cells to assist the complex cells, and/or replace the complex cells in order to correctly perform the assigned command. An improved method includes the steps providing a creation of the psychoconduction code based on the simplified symbols, which by the audio, video, kinesthetic and/or olfactory stimulation simple cells to correct or replace the complex cells. An improved system comprises a controlling system comprising a processing system, including a controller and a memory, and a terminal device comprising at least one of a compact disk driver, a floppy disk driver, a printer and a control panel. Also, the improved system comprises an auxiliary equipment and a display connected to the controller, which is connected to the speaker(s).

2 Claims, 30 Drawing Sheets

METHOD AND SYSTEM FOR PSYCHOLOGICAL TREATMENT BY BRAIN STIMULATION OF THE PSYCHOLOGICALLY DISORDERED OBJECT

FIELD OF THE INVENTION

This invention relates to the psychoconduction method and system intended for brain stimulation providing correction of the malfunctioning complex cell and/or replacement of the malfunctioning complex cell by the modified simple brain cells, and mostly relates to the calibration, balancing, alignment, and stimulation of the different parts of the brain using the different structures and pattern of the visual, audio and/or kinesthetic perception, and olfactory expressions having the same meaning.

BACKGROUND OF THE INVENTION

The various types of the methods and systems for psychological brain treatments and stimulations are well known in the medical and counseling practice. Some brain treating methods require placement of a probe and sensing, stimulating of the both areas of the brain, especially the intralaminar nuclei. Moreover, stimulation is controlled and offered when certain conditions within the area of interest are detected. Stimulation and sensing include electrical, chemical or combinations thereof. For example, the surgical principles (method) can be applied for "deep" psychological, neurological and/or psychiatric disorders. The surgical method has an extensive history. In the early 1930's, Fulton and Jacobsen first recognized that experimentally induced neurotic behavior in chimpanzees could be abolished by frontal lobectomy. Within a few years, Freeman and Watts developed the first psychosurgical procedure for humans known as the frontal lobotomy. As the inherent physiology of the frontal lobe became more evident, the original freehand procedure of Freeman and Watts became less and less extensive and efficient. By the late 1940's, the method of stereo-taxis, in which the patient's brain is modeled in 3-dimensional space for exquisite targeting accuracy, merged with lesioning techniques resulting in an even more efficacious and safe psychosurgical procedure. Further developments of stereotactic equipment have combined with novel advancements in functional and anatomic imaging as well as intraoperative electrophysiological mapping to encompass the state of the art in the neurosurgical treatment of neurological and psychiatric disorders today. While technologically improved and more precise, today's surgical lesioning techniques have the fundamental limitation of being inherently irreversible and are essentially a "one shot" procedure with little chance of alleviating or preventing potential side effects. In addition, there is a limited possibility to provide continuous benefits as the disease progresses and the patient's symptoms evolve. Within the field of neurosurgery, the use of electrical stimulation for treating "deep" psychological, neurological and psychiatric diseases, including such disorders as, for example, movement disorders, etc. has been widely discussed in the literature. In the latest time it has been considered that electrical and/or chemical stimulation holds some advantages over lesioning, inasmuch as lesioning can only destroy nervous system tissue. In many instances, the preferred effect is to electrically stimulate the increasing, decreasing, or blocking of the psychological or neuronal activity. Electrical or chemical impact might be useful in some ways to provide the stimulation and/or modulation of the brain target neural structures.

For instance, the methods by U.S. Pat. Nos. 6,708,064; 6,418,344 and 6,167,311 provide modulation of the brain to affect psychological or psychiatric disorders. The methods provide the treating neurological conditions by proper placement of a probe and sensing, stimulating of the both areas of the brain. Generally, the methods relate to modulating the pathological electrical and chemical activity of the brain by electrical stimulation and/or direct placement of neuromodulating chemicals within the corresponding areas of abnormal function and activity. In accordance with the inventions, the methods are the surgical treatment of psychiatric disorders (e.g. addictions/substance abuse, obsessive compulsive disorder, generalized anxiety disorder, panic attacks, social phobia, major depression, learning disorder, etc.) by implantation of stimulating electrodes and/or drug/chemical delivery micro infusion at the assigned locations.

More particularly, the methods include the following general steps of 1) implanting a device in contact with an intralaminar nuclei of the brain; sensing activity in the specific area of the brain, wherein the specific area of the brain is different than the intralaminar nuclei, and wherein the specific area of the brain is different than the intralaminar nuclei and the sensing activity occurs at a location distal from the device location; and operating the device to modulate the intralaminar nuclei in response to said activity to thereby affect the disorder associated with the specific area of the brain, or 2) placing an electrode in contact with an intralaminar nuclei of the brain and operating the device to provide stimulation to the intralaminar nuclei to thereby affect the psychiatric activity in the specific area of the brain, the specific area of the brain being different than the intralaminar nuclei.

Such methods are not completely saved considering possible malfunction of the electrical/electronic equipment (e.g., higher electrical signal), that might lead to the critical destruction of the brain nervous tissue/cell.

Another method of brain stimulation is described in the U.S. Pat. No. 6,556,868. The method provides the treatment of psychological disorder consisting the group of memory impairment, a learning disorder, impairment of cognitive processing speed, impairment of acquisition of perceptual skills, impairment of acquisition of motor skills, and impairment of perceptual processing. In general, the method comprises the steps of: selecting an appropriate human (or animal) subject and applying to the subject's vagus nerve an electrical stimulation signal having parameter values effective in modulating the electrical activity of the vagus nerve in a manner so as to modulate the activity of preselected portions of the brain. The stimulating electrical signal has to be effective to cause a physiological, structural or neuronal connective alteration in the brain. Neural function in the brain is changed as a consequence of the neuronal connective alteration; thereby changing behavior, or the capacity for behavior, in the human or animal subject.

This method has the same deficiency as the previous patented method, i.e. the electrical stimulation is not completely saved considering possible malfunction of the electrical/electronic equipment (e.g., higher electrical signal), that might lead to the critical destruction of the brain nervous tissue/cell.

The other known devices (U.S. Pat. Nos. 6,520,905 and 6,798,898) also use the portable biosensor. The described in these patents methods classify an individual's personal preference for an image. In common the methods comprise the steps of: viewing an image for a period of time; ranking the image on a scale extending between a "detached" feeling and an "attached" feeling, where "detached" is a feeling of not being able to personally connect to the object or situation depicted in the image, and "attached" is a feeling of a personal connection to the object or situation depicted in their image; providing a portable device having at least one sensor for monitoring a physiological state of an individual carrying the device; recording at least one sensed physiological state over a period of time; analyzing the recorded physiological data to predict the individual's psychological and physiological state; and alerting the individual if the predicted state is determined to require management of said state. A portable biometric device is worn or carried by a user and which senses and records physiological parameters on a continuous basis. A biometric analyzer extracts the physiological activation state of user from one or more measured physiological parameters. A cognitive analyzer which extracts cognitive state from cognitive responses to images. A personal profiler which combines the physiological and cognitive measures obtained from the biometric analyzer and cognitive analyzer to generate an individual's personal image profile for a given state response.

These methods using the principles of the wearing/carrying of the portable device (sensors) can bring the additional stress and discomfort to the psychologically disordered individual, and again include in some way the mentioned above deficiency inherent in electrical contact of the electrical equipment (sensors) with the human body, that might be not completely saved considering the possible malfunction of the electrical/electronic equipment, that might lead to the possible injury. Also, these methods can provide recognition of the individual's physiological and psychological state, but does not provide brain (cell) stimulation (treatment), e.g. such as improving memory and learning capabilities.

The U.S. Pat. No. 6,433,977 discloses the apparatus and method for changing critical brain activity using light and sound, exposing the patient to one or more lights placed in close proximity to a patient's eyes wherein the one or more of that lights selectively stimulate the non-dominant eye connected to the non-dominant cerebral hemisphere. The apparatus is presented either by a device that covers the patient's eyes, such as a pair of sunglasses, or devices including sports helmets that are used to protect players' craniums and may be integrated into the protective head gear (e.g., football, bicycle helmets, etc.). Also, the device can include the computer monitors and televisions, which are able to encompass one or more oscillating lights set-up in a proscribed manner on a person's monitor. The light may be displayed in a subliminal alternating checkerboard pattern that would be set to the individual user. The light stimulates the non-dominant cerebral hemisphere greater than the dominant cerebral hemisphere. In this version, the non-dominant cerebral hemisphere is stimulated to a greater degree than the dominant cerebral hemisphere. It is the coordinated stimulation of the non-dominant hemisphere that helps create a balance of integration of excitatory post synaptic potentials (EPSP). The apparatus for selectively stimulating the non-dominant cerebral includes a surface placed in close proximity to a patient's eyes and one or more lights disposed on the surface. The one or more lights stimulate the eye connected to the non-dominant cerebral hemisphere to a greater extent than the eye connected to the dominant cerebral hemisphere at a rate of approximately, e.g., 60/40. By overstimulating the non-dominant hemisphere there is an increase in the patient's ability to maintain a heighten mental status, and in turn sets up for a globality of the increased muscular activity. Alternatively, the surface may be sleeping goggles or the glasses reflecting the light from a source next to the eye (light is reflected from the glass surface) into the patient's eyes.

These method and device are not able to provide an improvement of the individual's learning processes, such as mathematics, alphabet, etc.

Thus, there is a great need in the art for the improved method and system for psychological treatment by brain stimulation of the psychologically disordered object, employing at the same time the correction of the malfunctioning complex cell and/or replacement of the malfunctioning complex cell by the modified simple brain cells, and providing possibility to balance, align and stimulate of the different parts of the brain using different structures and pattern of visual, audio and/or kinesthetic perception, and olfactory expressions having the same meaning.

OBJECT AND ADVANTAGES OF THE INVENTION

Accordingly, several objects and advantages of the present invention are to provide an improved brain psychological treatments, such as calibration, balancing, alignment and stimulation of the different parts of the brain of the psychologically disordered object.

It is another object of the invention to modify the simple brain cells in order to provide correction or replacement of the complex cell.

It is still another object of the invention to provide video patterns (images) expressed in the visual symbols stimulating brain cells.

It is further object of the invention to provide audio patterns expressed in the adequate sound symbols stimulating brain cells.

It is still further object of the invention to provide kinesthetic patterns expressed in the individual's body and/or object movements stimulating brain cells.

It is still further another object of the invention to provide olfactory patterns expressed in the smells stimulating the adequate brain cells.

It is another further object of the invention to provide the enhancement of the existing structure, restructurization of the tune, calibration and recalibration of the different brain areas without any surgical and/or pharmacological/chemical interventions.

It is still another further object of the invention to improve learning possibility and skills of the psychologically disordered object.

Still, further objects and advantages will become apparent from a consideration of the ensuing description accompanying drawings.

DESCRIPTION OF THE DRAWINGS

In order that the invention and the manner in which it is to be performed may be more clearly understood, embodiments thereof will be described by way of example with reference to the attached drawings, of which.

SUMMARY OF THE INVENTION

The method and system for psychological treatment by brain stimulation of the psychologically disordered object provide a possibility to stimulate the simple cells to assist the complex cells, and/or replace the complex cells in order to correctly perform the assigned command.

The psychoconduction uses the psychodynamic approach. For example, the verbal expressions create a catharsis of the emotional reaction during the psychotherapy session. This approach is based on the congruent processing of the verbal and emotional information. When a psychologically disordered object is experiencing anger and frustration, the body sensations or kinesthetic functions take over of all other functions. It manifests itself in the heart palpitation increasing, muscles tension and rapid breathing. In the condition of anger and frustration, the object's movement, verbal, and audio communications in this state of mind get down to a very simple level. An object (e.g. an individual or a person) in this state uses the simple movements, has difficulty using the verbal expressions, and has difficulty understanding audio information. In such condition the object reacts only on simple audio or video signals. In this state the complex cells do not work and the communication is possible on a very simple level only.

The psychologically disordering (and sometimes psychotic) symptoms are mainly related to different hallucinations. The audio or visual hallucinations take over the object's life. The stressed or depressed object may not have hallucinations, but have the flash backs and nightmares. The hyperactive objects have the exaggerated kinesthetic functions. They are not in control of their desired fast movements, restless appearance, fidgeting, and the rapid speech activities. For instance, if kinesthetic response does not support the exaggerated reaction, visual and/or audio information can be adjusted by kinesthetic response.

An improved method includes the steps providing a creation of the psychoconduction code based on the simplified symbols, which by the audio, video, kinesthetic and/or olfactory stimulation simple cells to correct or replace the complex cells. An improved system comprises a controlling system comprising a processing system, including a controller and a memory, and a terminal means comprising at least one of a compact disk means, a floppy disk means, a printing means and a control panel. Also, the improved system comprises an auxiliary equipment and a display connected to the controller, which is connected to the speaker(s).

DESCRIPTION OF THE PREFERRED EMBODIMENTS

Here the description of an improved system will be done in statics (as if the components of the improved lifting system are suspended in the space) with description of their relative connections to each other. The description of the method and functional operations of an improved system will be done hereinafter.

Figure 1:
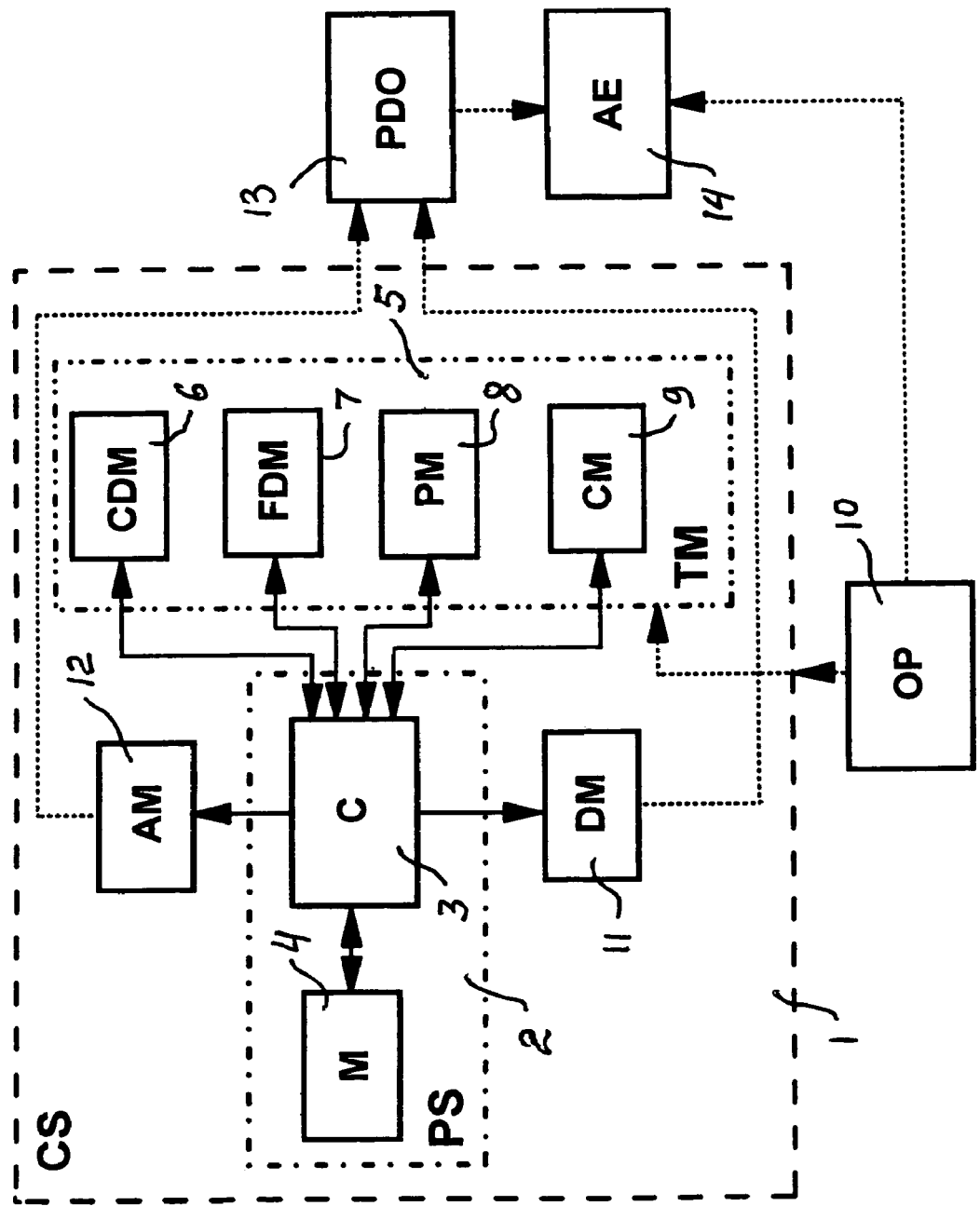
FIGS. 1, 2 are the simplified block-schemes of the apparatus realizing the psychological treatment by brain stimulation of the psychologically disordered object.

According to FIG. 1, the apparatus realizing the psychological disorder treatment includes a controlling system (CS) 1 comprising a processing system (PS) 2, including a controller (C) 3 and a memory (M) 4, and a terminal means (TM) 5 comprising at least one of a compact disk means (CDM) 6, a floppy disk means (FDM) 7, a printing means (PM) 8 and a control means (CM) 9, for example, such as key board, mouse, etc. The terminal means 5 can also include, for example, a scanning means (not shown), video camera (not shown), microphone (not shown), etc. The terminal means 5 of the controlling system 1 is controlled by an operator (OP) 10, who can, for example, be represented by psychologist. Also, the controlling system 1 comprises a displaying means (DM) 11 connected to the controller 3, which is also connected to an audio means (AM) 12. Also, the controller 3 is connected to the memory 4 of processing system 2, and to the compact disk means 6, floppy disk means 7, printing means & and to the control means 9 of the terminal means 5. The sonic information (e.g. sound/psychoconduction sonic combination/) produced by the audio means 12 and/or video information (e.g. image/psychoconduction visual (symbol) combination) by the displaying means 11 are perceived by an psychologically disordered object (PDO) 13. The psychologically disordered object 13 can be supported by an auxiliary equipment (AE) 14, additional training devices, means, such as, for example, step board for kinesthetic skill improvement or calculator, pencil, pen, etc. for learning skill improvement, etc. The auxiliary equipment 14 is selected by the operator 4 in compliance with the assigned treatment.

Figure 2:
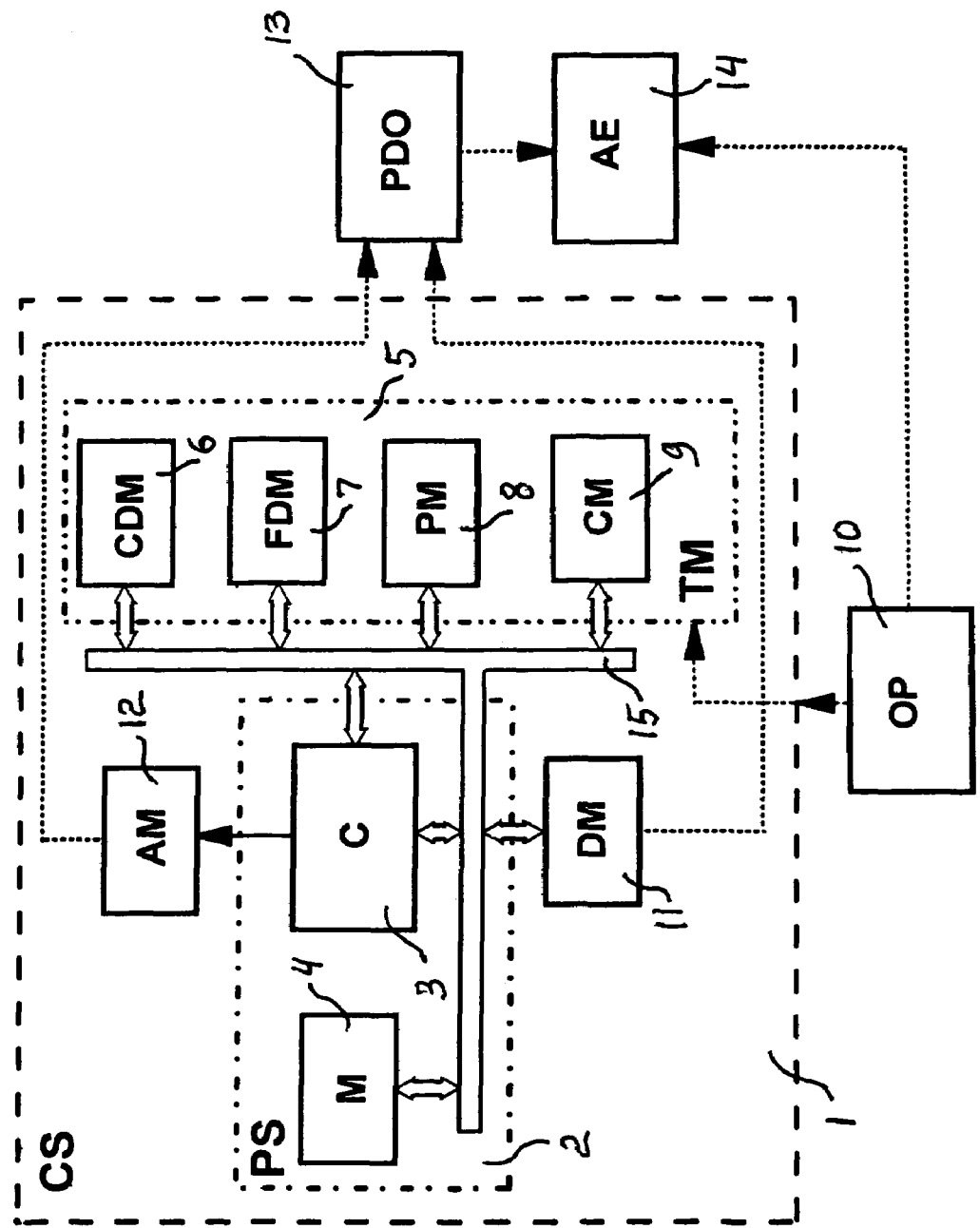

Referring to FIG. 2, the some connections between blocks (components/means) of the controlling system 1 are presented by a multiplexed bus 15.

An improved method provides a psychological brain stimulation treatment of the psychologically disordered object by psychoconduction. The psychoconduction method is a sequence of the operations (steps) intended for correction and enhancement of the brain capacity. An improved method (process) provides the enhancement of the existing structure and restructurization of the tune, calibration and recalibration of the different brain areas. Psychoconduction allows simple cells act as the complex cells within the different areas of the brain. The substitution of the complex cells by the simple cells might be compared to the steam cells. Also, the improved method (psychoconduction) reinforces the addresses to provide access to the complex cells for the appropriate stimuli processing. The brain structure uses the simple cells of the brain in order to process the simple stimuli (symbol), and the more complex cells are used to process the more complex stimuli. Psychoconduction provides the simple stimuli utilizing the simple brain cells. Many disorders are caused by deficiency of the brain to process the visual, audio, kinesthetic and olfactory information correctly. The results of such disorder might be the confusion, misunderstanding, anxiety, despair anger overreaction, and/or learning disabilities. The described difficulties lead to the inability of the impaired or underdeveloped complex brain cells to process complex information correctly. Normally, the visual, audio, kinesthetic and/or olfactory stimulus causes a nerve impulse to travel down the axon to the synapses where the pulse triggers the release of the chemical messenger molecules, for example, such as dopamine, SSRI, and non-epinephrine for a correct reaction. If the stimulus is complicated (e.g. because of the ambivalent information) the impulse travels down the axon to the incorrect location. This is the reason why the impaired complex cells are not provided with the authentic information.

The areas of the brain that are involved for the vision are the occipital, parietal and temporal cortexes. The brain area processing the sonic (audio) information includes the primary auditory cortex (PAC) in the superior temporal gyrus of the temporal lobe. The kinesthetic stimulus is processed in the cerebellum that is responsible for the appropriate action according to the motor commands.

The olfactory stimulus is processed in the olfactory mucosa (OM). The olfactory mucosa processes the different odors. The improved method (process) uses only the simple cells in the areas that are responsible for the simple stimulus processing. Psychoconduction stimulates the different brain areas by the simple symbol only. That simple symbol can be the visual, audio, kinesthetic and/or aroma. Psychoconduction provides processing of the simple symbol instead of the complex symbol. Psychoconduction enhances the brain capacity by stimulation of the brain and gradually increases different patterns of the simple symbol using the simple cells of the brain, that usually processes the simple information. Psychoconduction provides stimulation of the different parts/areas of the brain by the same patterns. For example, the psychoconduction method provides translation (interpretation) of the kinesthetic symbols to the audio and/or visual symbols. During translation the areas of the brain, which process the kinesthetic symbol, is attuned with the ones in the brain area that reproduces the visual and/or audio symbol. In the improved method (psychoconduction), the same pattern of the simple symbol processing provides the congruence of the chemicals released by the different areas of the brain. This part of the improved method is similar to the brain biofeedback while the brain corrects itself and creates the equilibrium between different brain areas in response to the same stimulus. Psychoconduction is intended for correction of the inappropriate responses to the stimulus. For instance, when one area of the brain used for information (e.g. sonic information) processing is affected by the distortion, there is a high probability that the information might be distorted and improperly processed. As a consequence, an inappropriate response may lead to the overreaction and/or underestimation of the original information. In order to correct the problem, the psychoconduction uses the pattern that is transformed in the codogram (Litvin's code). The simple symbol presented by such codogram stimulates the different parts of the brain and enhances the brain learning capability and capacity. The codogram with the same patterns of the simple symbol creates the connection between different parts of the brain and utilizes the similar molecular structure for stimulation of the different parts of the brain with the similar patterns of the molecular messenger.

Figure 3:
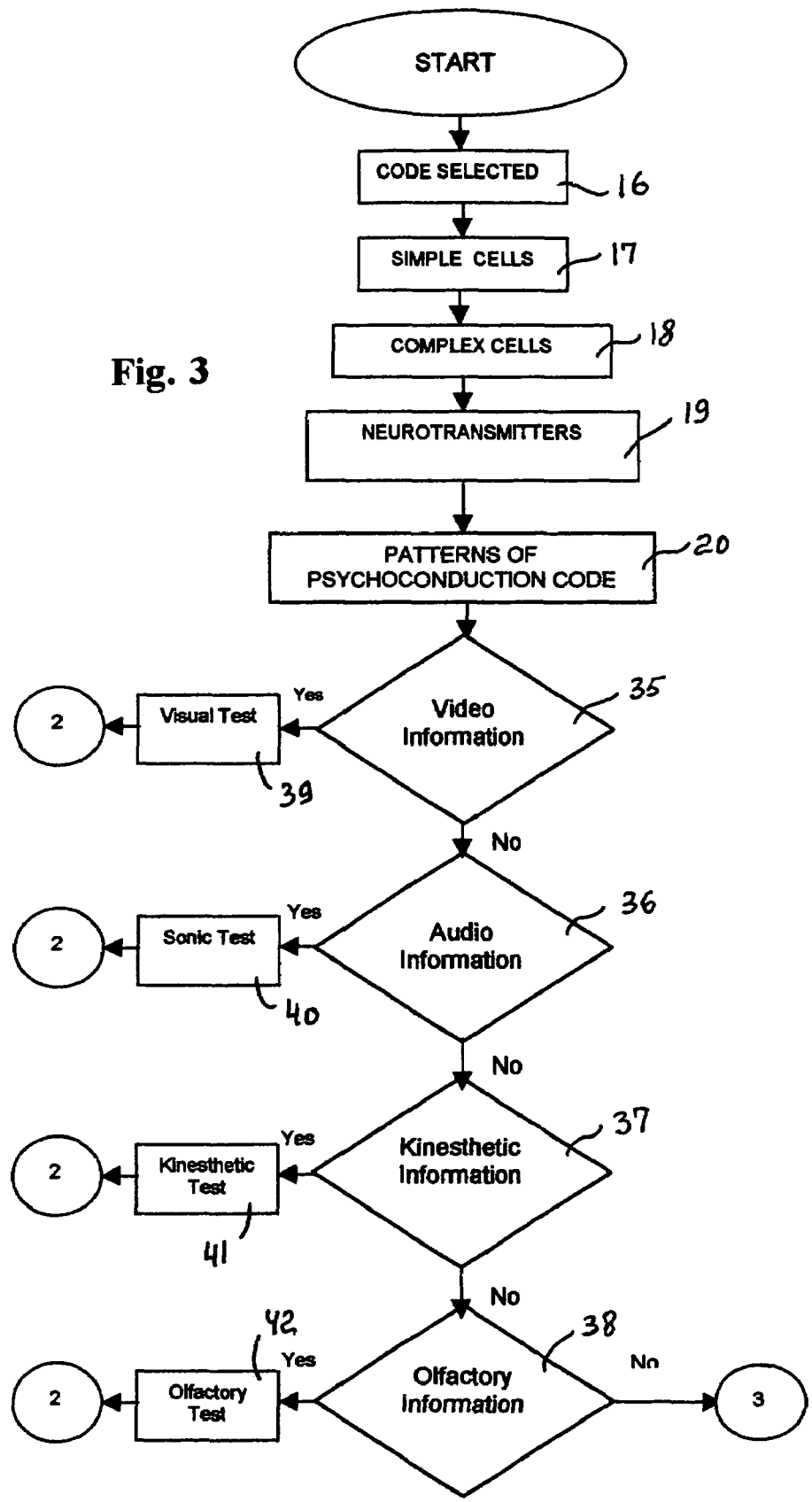
FIG. 3 is a simplified flow-charts illustrating the method for psychological treatment by brain stimulation of the psychologically disordered object.
Figure 3:
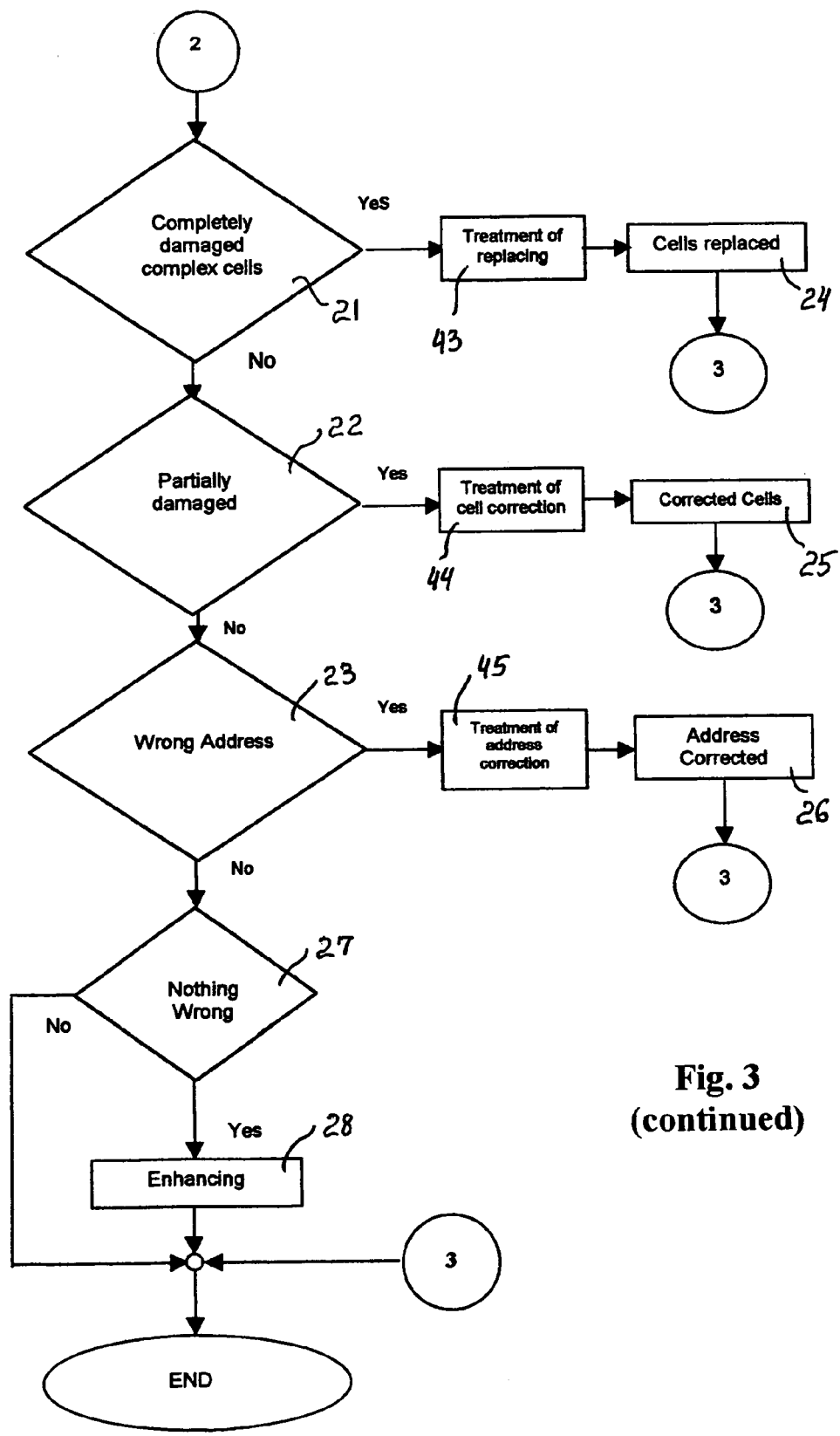

The FIG. 3 illustrates the psychoconduction method, including the steps of selection of the psychoconduction codogram (code) in order to use the simple symbol providing a simple stimuli 16 for activation of the simple cell 17 and the complex cell 18 to process the selected codogram. After processing, the neurotransmitters are released 19. Using the different modes of perception, the pattern of psychoconduction is acquired 20. The steps 35-38 provide the selection of the appropriate test, for example, such as visual test 39, sonic test 40, kinesthetic test 41, olfactory test 42, tactual test (not shown), etc., to evaluate the type of the psychological disorder. The improved method allows to distinguish the disorder category, such as either the complete damage to the complex cells 21, or partial damage 22, or the misaddressing of the command (stimuli) 23. Considering the damage to the complex cells 21, the perception of the codogram/cell replacement treatment 43)/activates the replacement of the complex cell by the simple cell (block 24). If the partial damage 22 is detected, the psychoconduction (codogram) provides correction/cell correction treatment (44)/of the complex cell by a simple cell 25. According to the command misaddressing disorder 23, after address correction treatment 45 the simple cell assists (block 26) to define the complex cell responsible for the address processing in order to submitted stimuli be correctly processed. The psychoconduction provides the possibility to enhance the complex cells 28 by the simple cells 27, if the psychological disorder is evaluated as not extremely deep 27.

Figure 4:
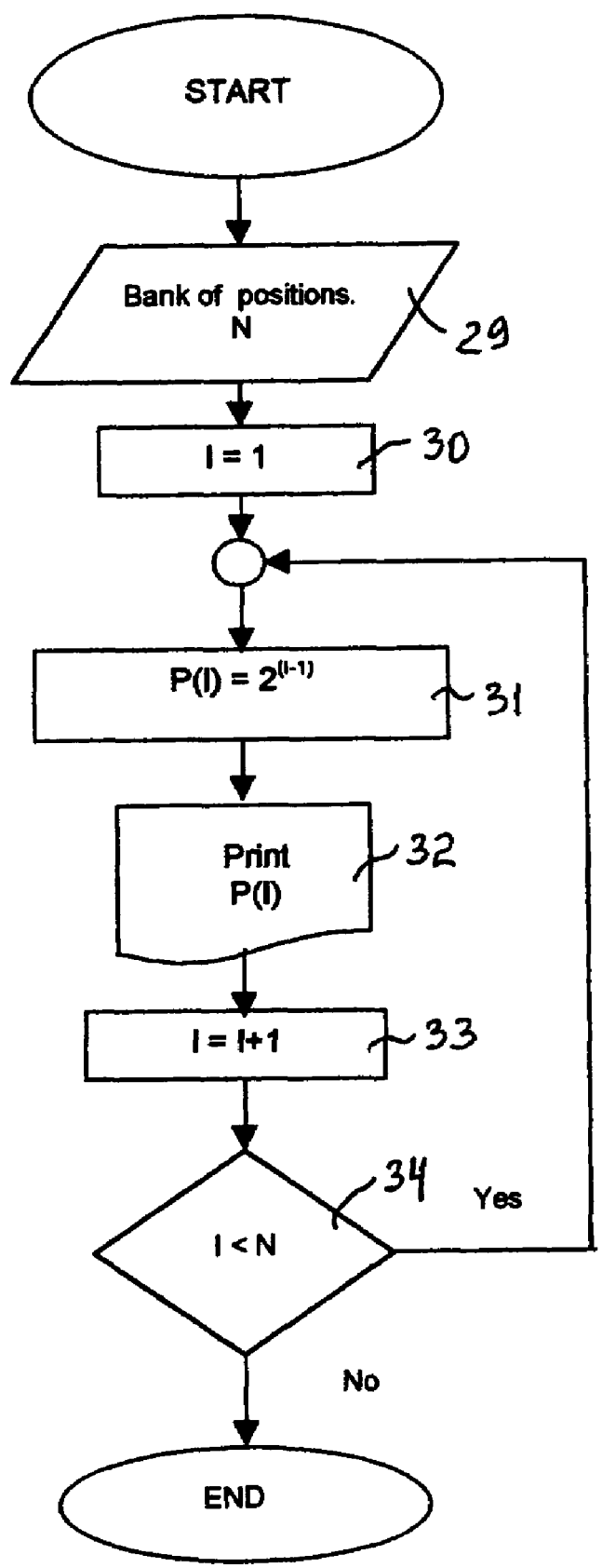
FIGS. 4, 5 are the simplified flowcharts illustrating the method for psychological treatment by brain stimulation of the psychologically disordered object in the vectorial principles of the psychoconduction steps.

In FIG. 4 is shown the vectorial analysis for psychoconduction steps (operations) during codogram (psychoconduction code) formation for brain stimulation of the psychologically disordered object. According to the block 30 of the value ("weight") calculation method shown in FIG. 4, the initial position $N_i=N_1$ (i=1, 2, 3, . . . , n−1, n) of the vectors $\vec{P}_j$ is selected from the bank 29 of positions $N_i$. The value ("weight") of the initial vector is $\vec{P}_j=\vec{P}_i$ (j=1, 2, 3, . . . , m−1, m). The cyclical process of the codogram value evaluation is illustrated by the blocks 31-34 in accordance with the equation $$\vec{P}_j=b^{(j-1)},\qquad [1]$$

wherein "b" is a codogram basis.

The basis "b" for the psychoconduction code and pattern creation can be a basis of any recognizable codes including reversibility of the codes (their "mirror" image/order representation, e.g. ascending/descending order) and their combinations. For instance, psychoconduction code can be presented from left to right, from right to left, from top to bottom or from bottom to top, and their combinations. As, for example, it will be shown hereinafter the binary code basis (b=2) has been presented in the further disclosure.

Figure 5:
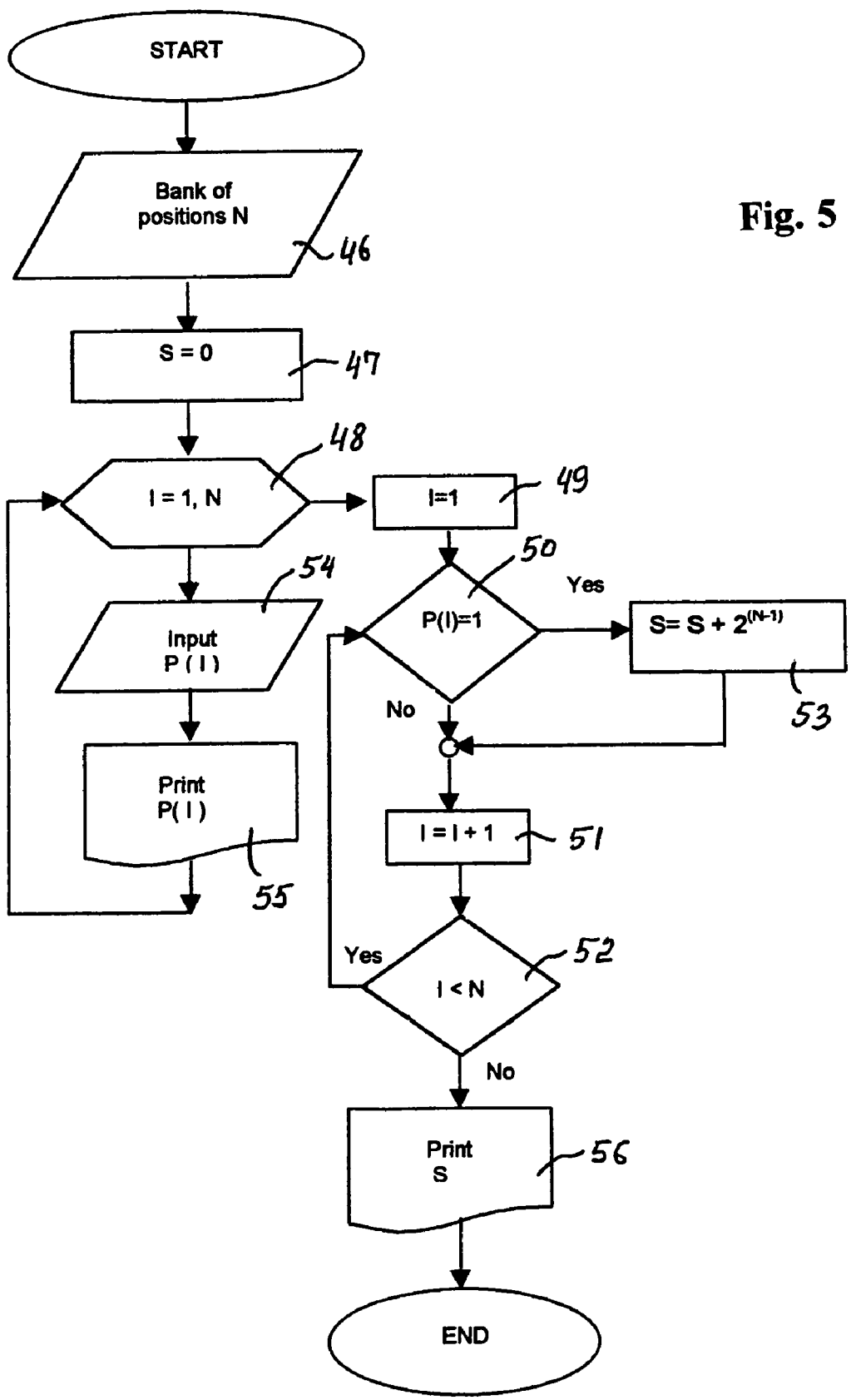

According to the block 47 of the method of numbers calculation shown in FIG. 5, the initial sum $S_{j=0}$ for initial position $N_i=N_1$ of the vectors $\vec{P}_j$ from the bank 46, considering as has been described of the above for i=1;n.

The psychoconduction code (codogram) creates the different value (weight) $\vec{P}_j$ of the codogram positions, for example, it is conditionally assumed that "a full" position is equal to "1" and "an empty" position is equal to "0 (zero)". Additionally it is assumed, that for visual perception of the psychologically disordered object the "full" position can be represented, for instance as ("x"), ("1"), dot or as a dark geometrical figure, such as dark color circle, square or rectangle, etc. and the "empty" position can be represented, for instance as a circle ("o"), "0 (zero)", or as a light geometrical figure (e.g. such as light color circle, square or rectangle, etc.).

Hereinafter, the symbolic "full" ("1", "x", etc.) and "empty" ("0", "o", etc.) will be used in the text of the disclosure, and the "dot" in the rectangle will represent the meaning "full" and empty rectangular (no dot) will represent the meaning "empty" in the illustrations shown in FIGS. 13-18.

Referring to block 49, the first position is equal to "1". Blocks 50-52 provide iteration of the possible positions $N_i$ with the calculation $S_k$ (K=1;k) for each full position (see block 53). Block 54 provides the input of the sequential vector $\vec{P}_j$, and blocks 55 and 56 provide the printout of the resulting information.

Figure 6A:
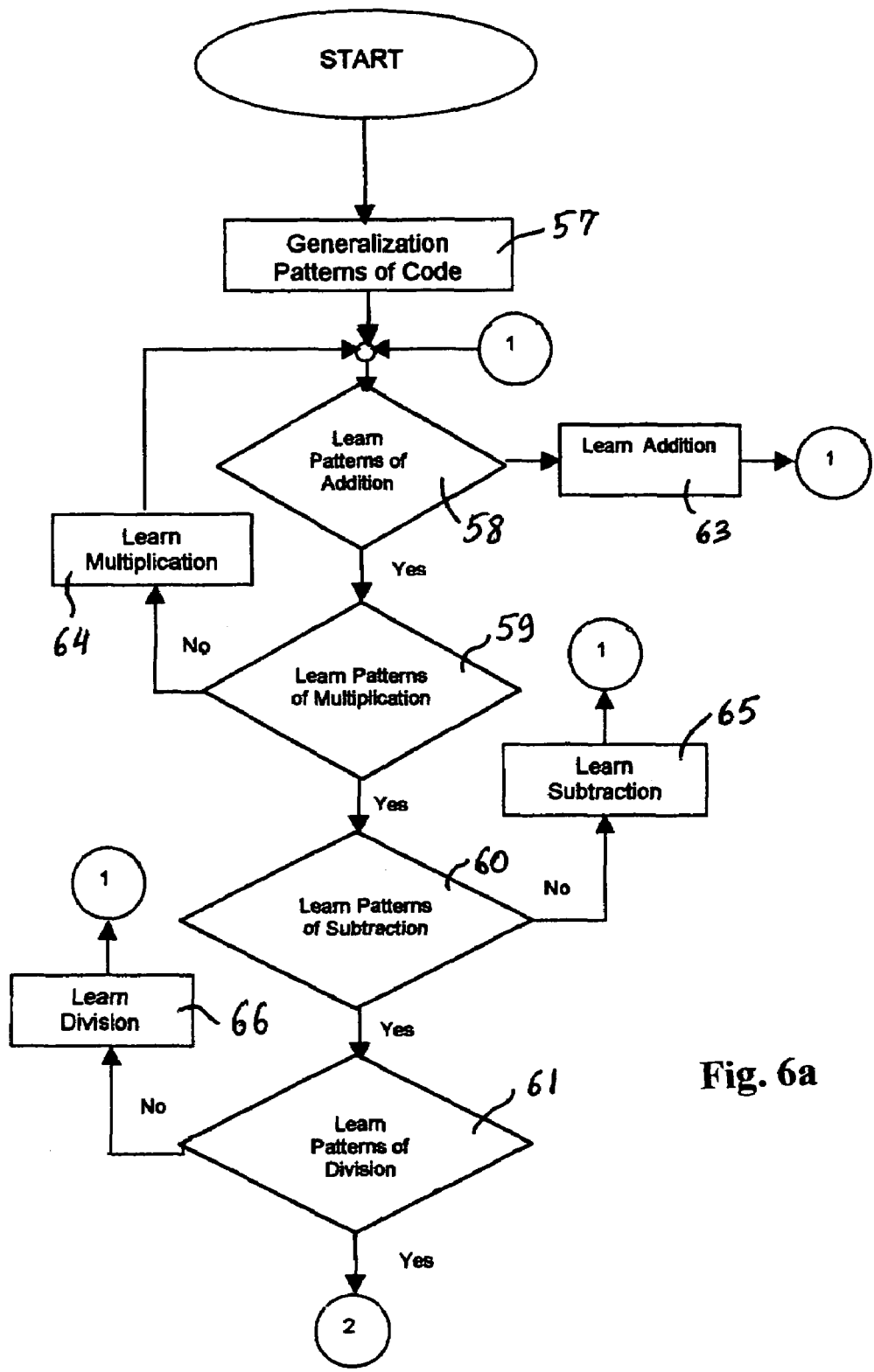
FIGS. 6a-6d are the simplified flow-charts illustrating the method for brain stimulation of the psychologically disordered object by kinesthetic, audio, video, and/or olfactory treatment respectively.
Figure 6A:
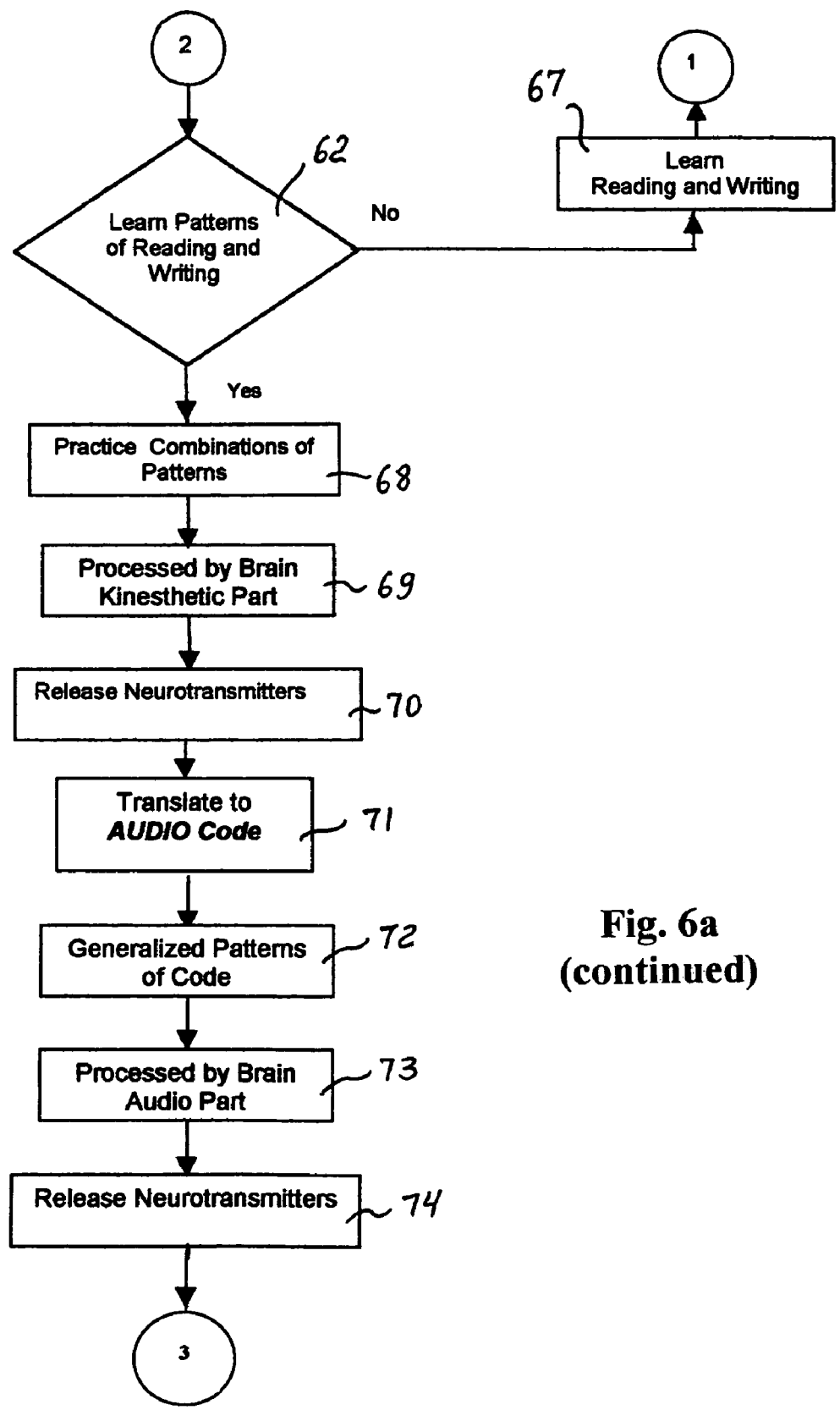
Figure 6A:
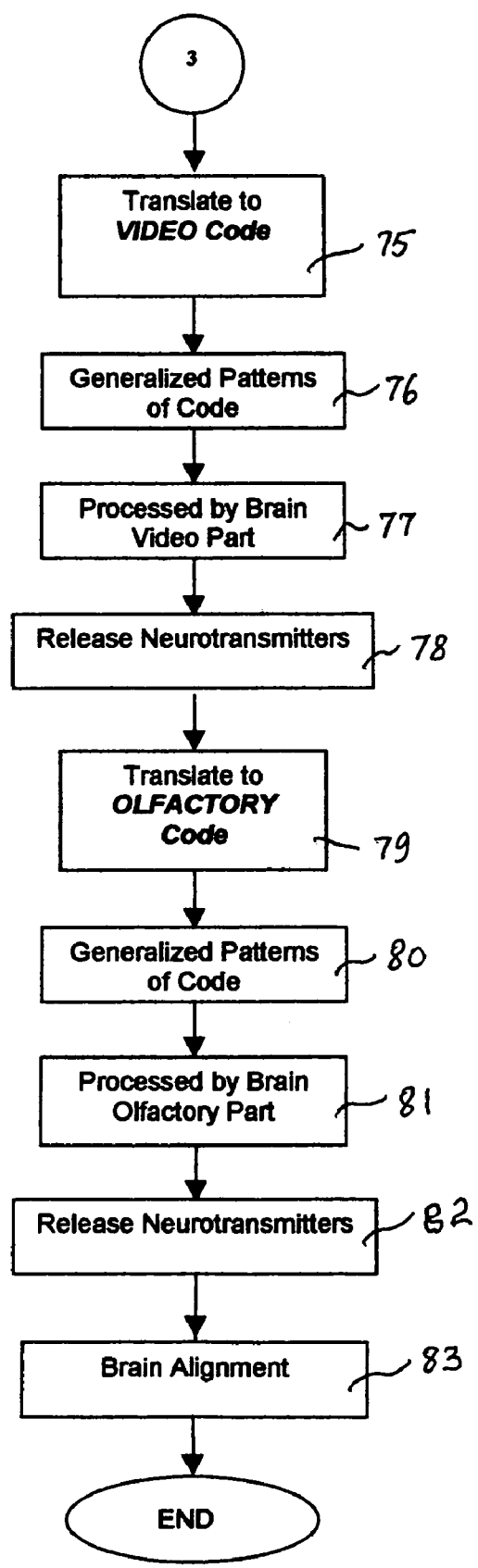
Figure 6B:
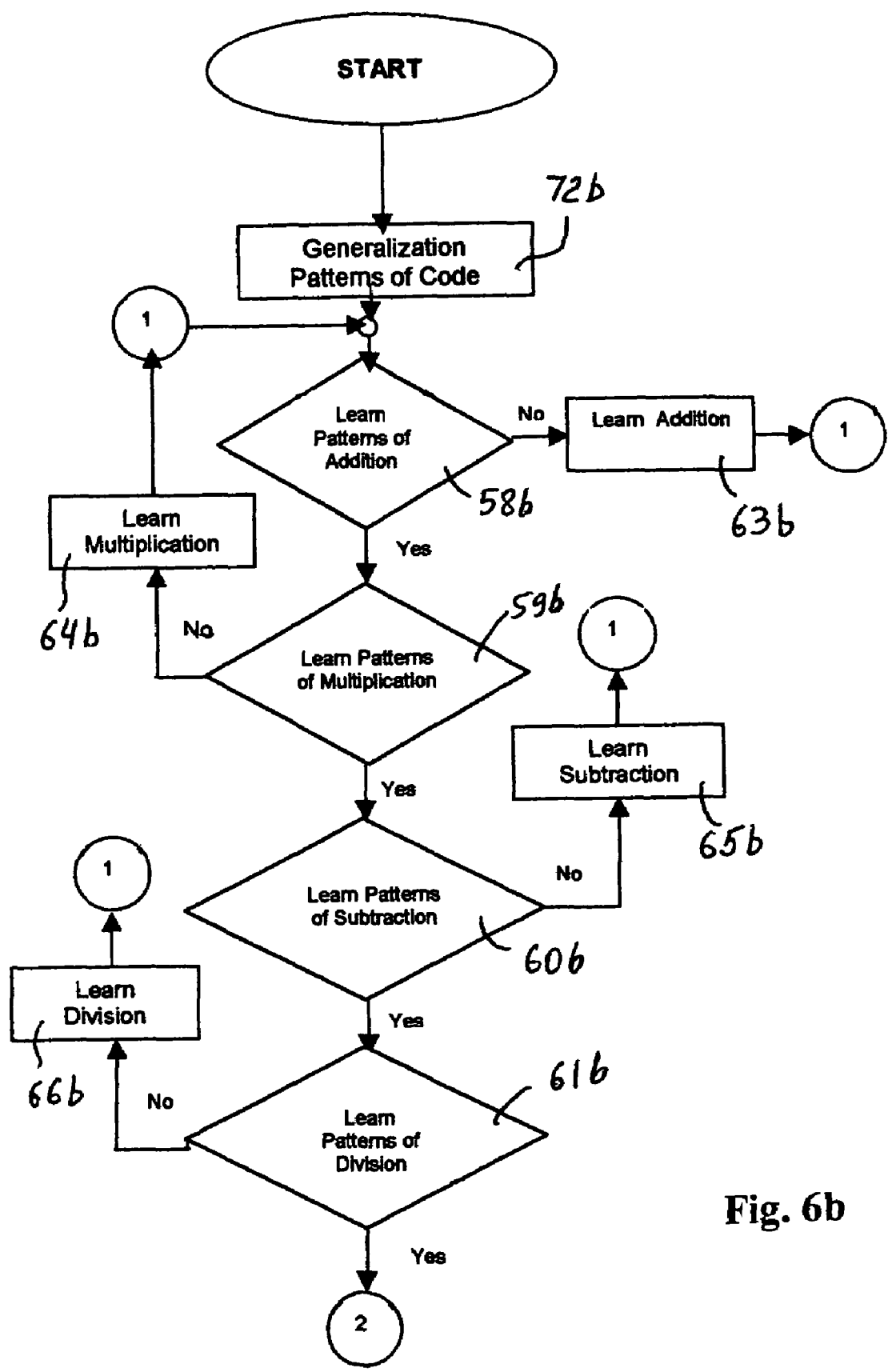
Figure 6B:
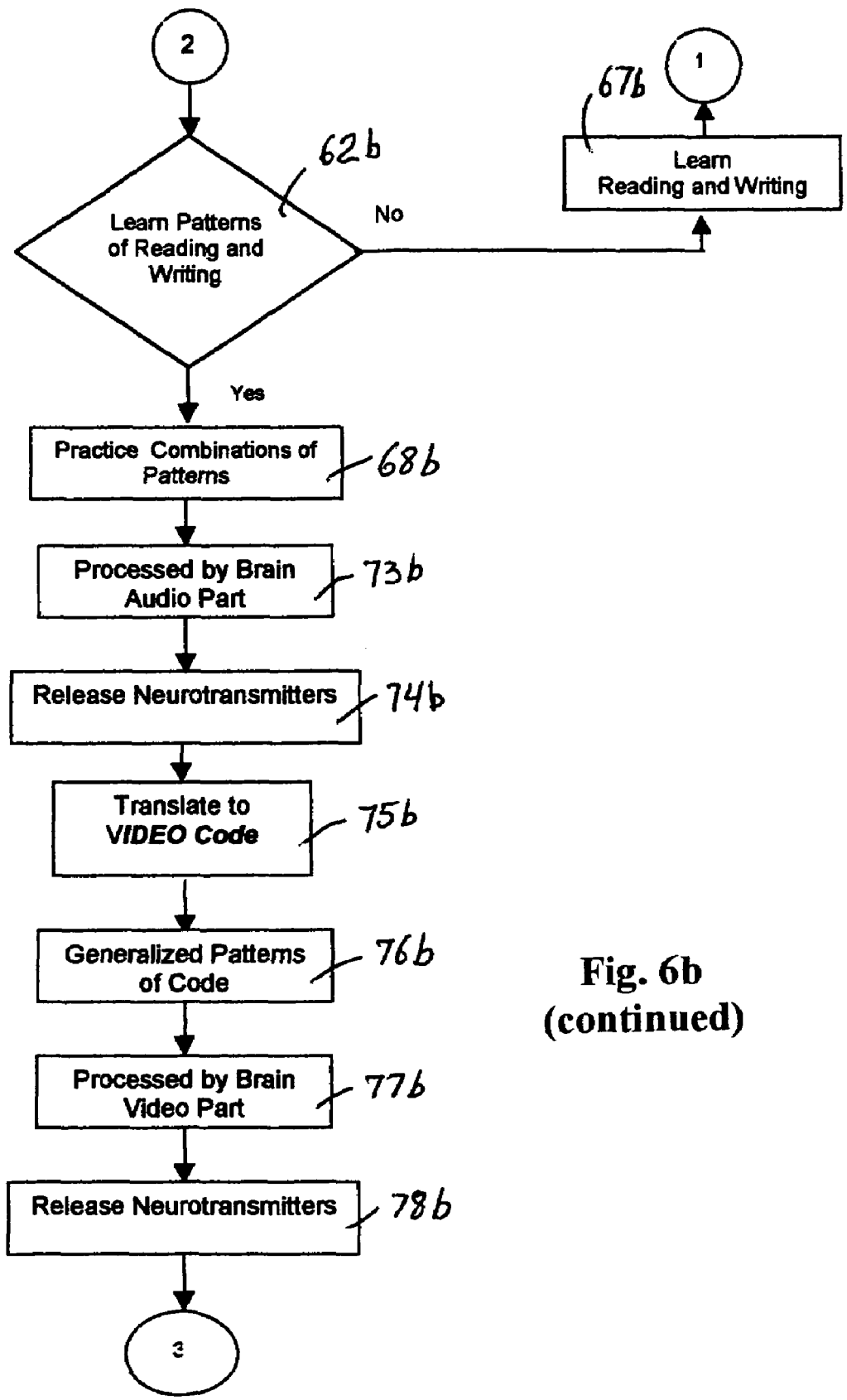
Figure 6B:
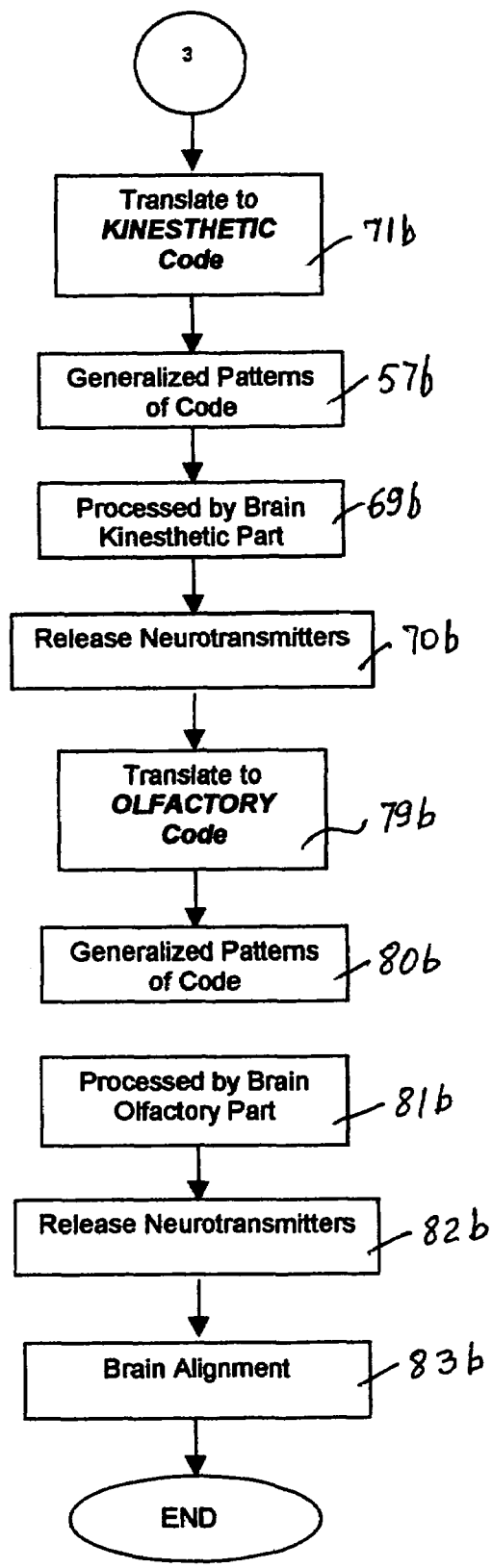
Figure 6C:
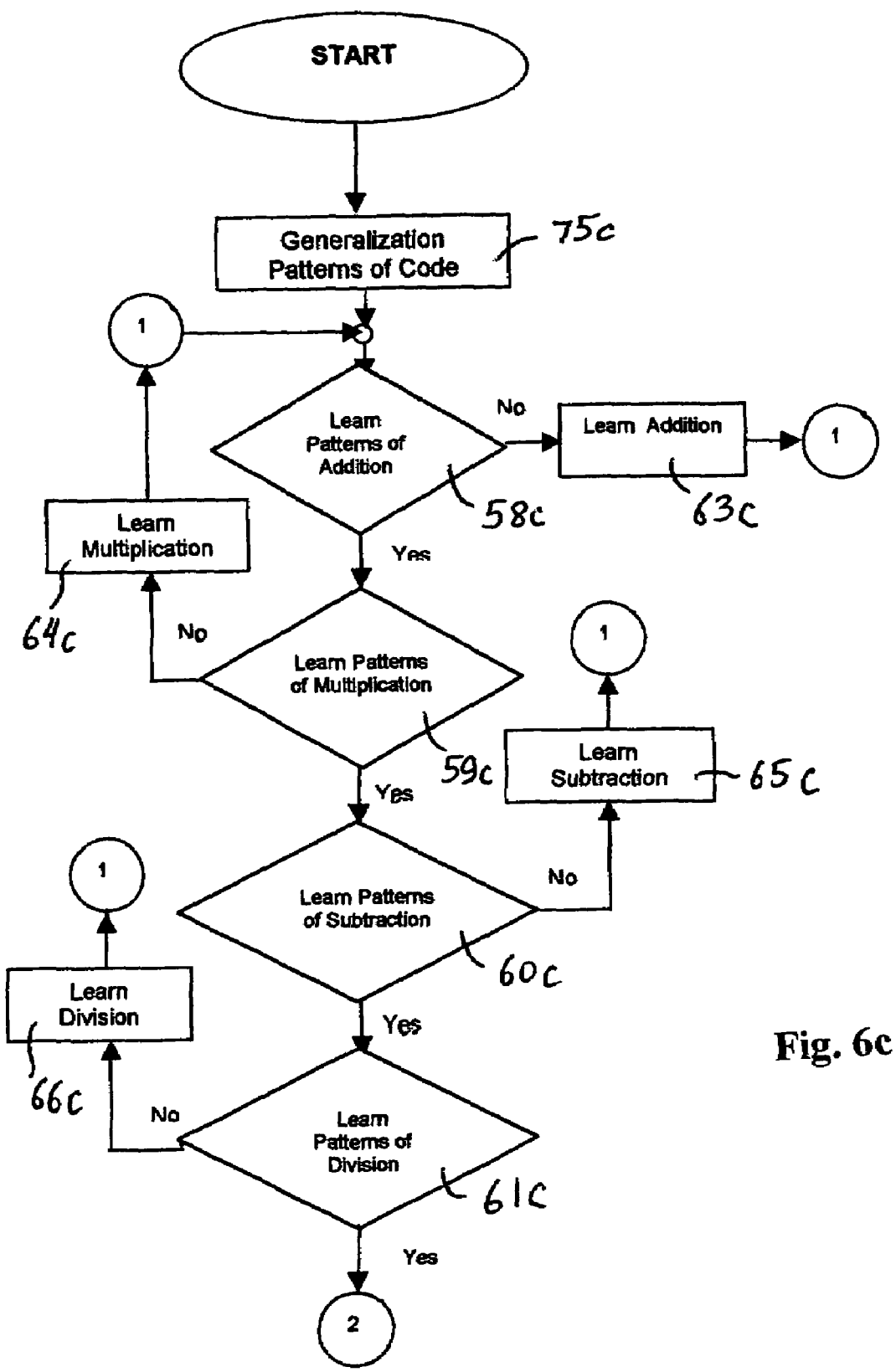
Figure 6C:
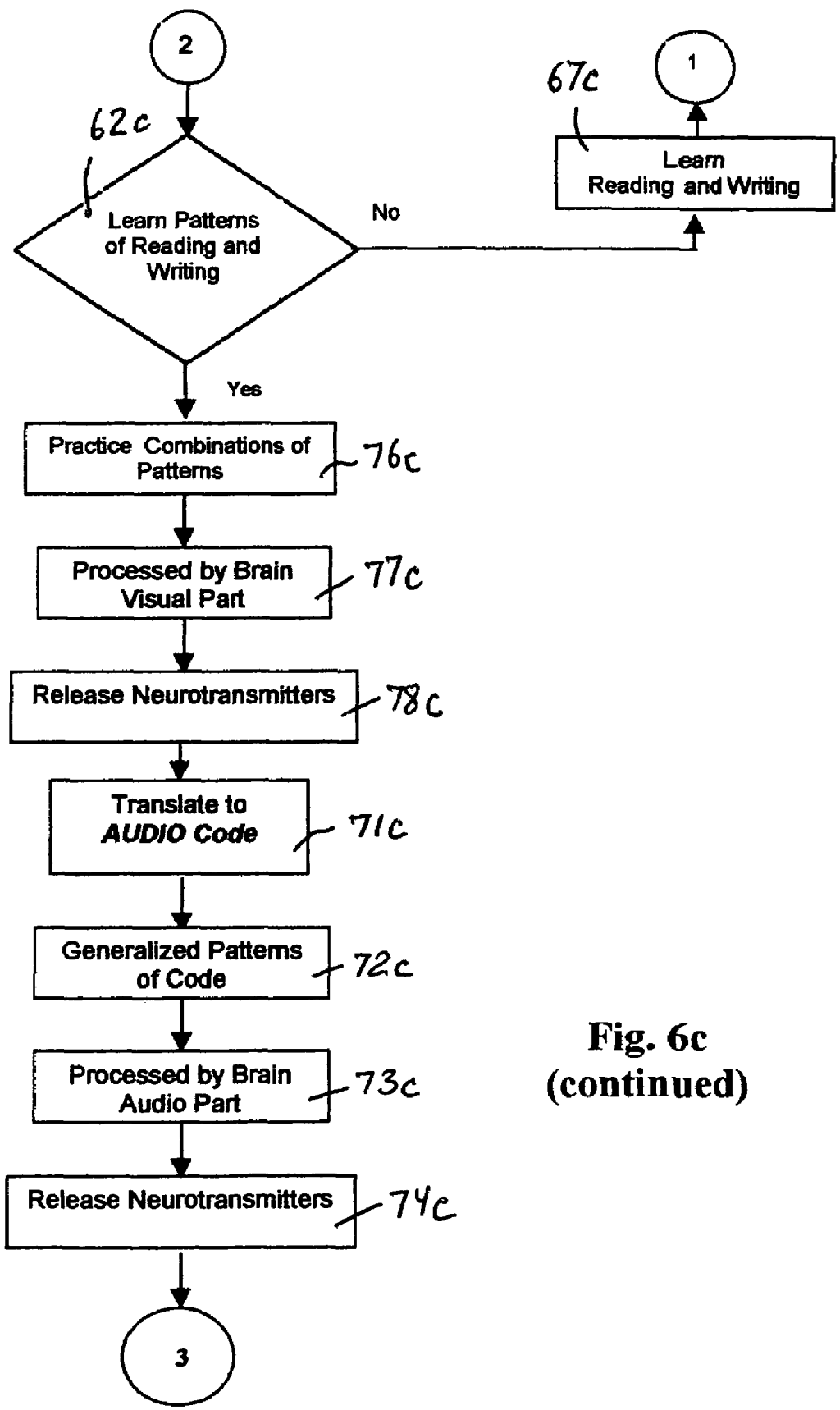
Figure 6C:
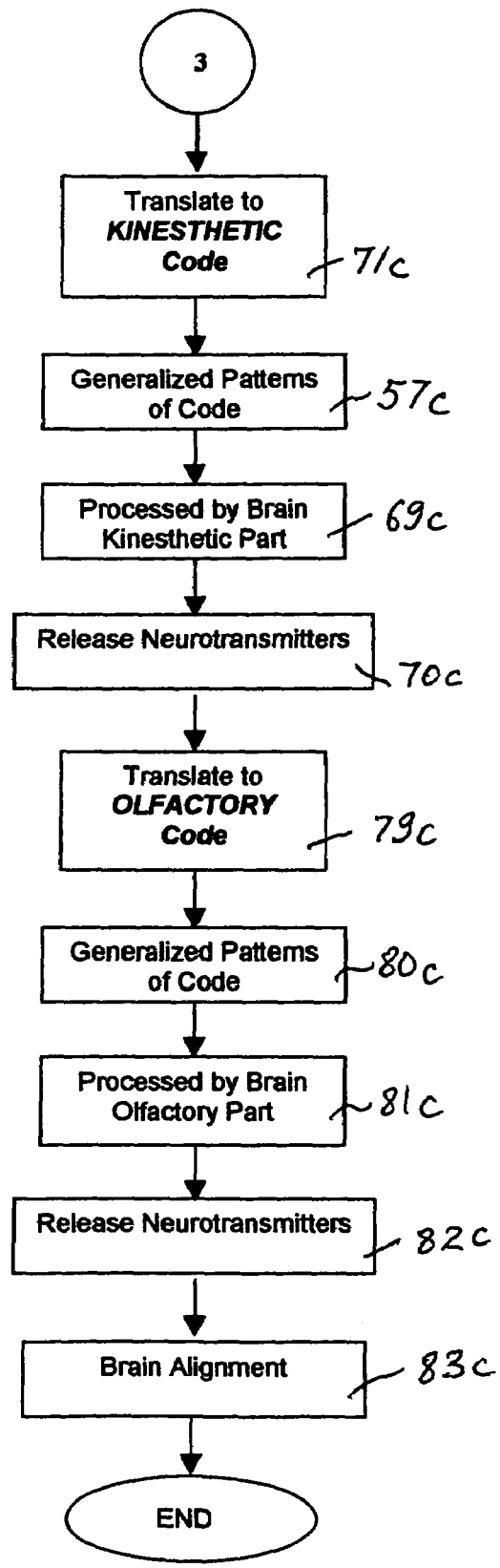
Figure 6D:
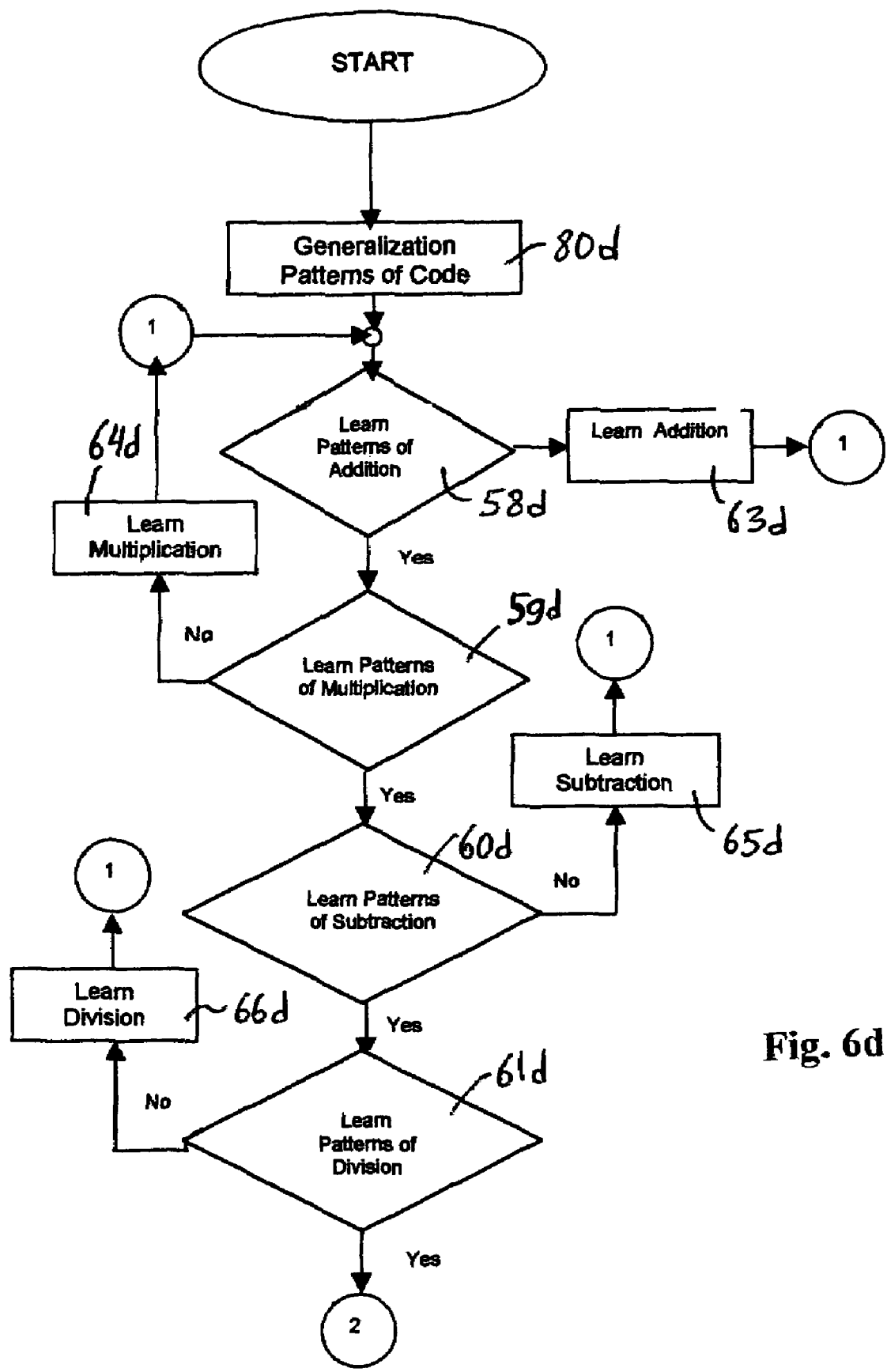
Figure 6D:
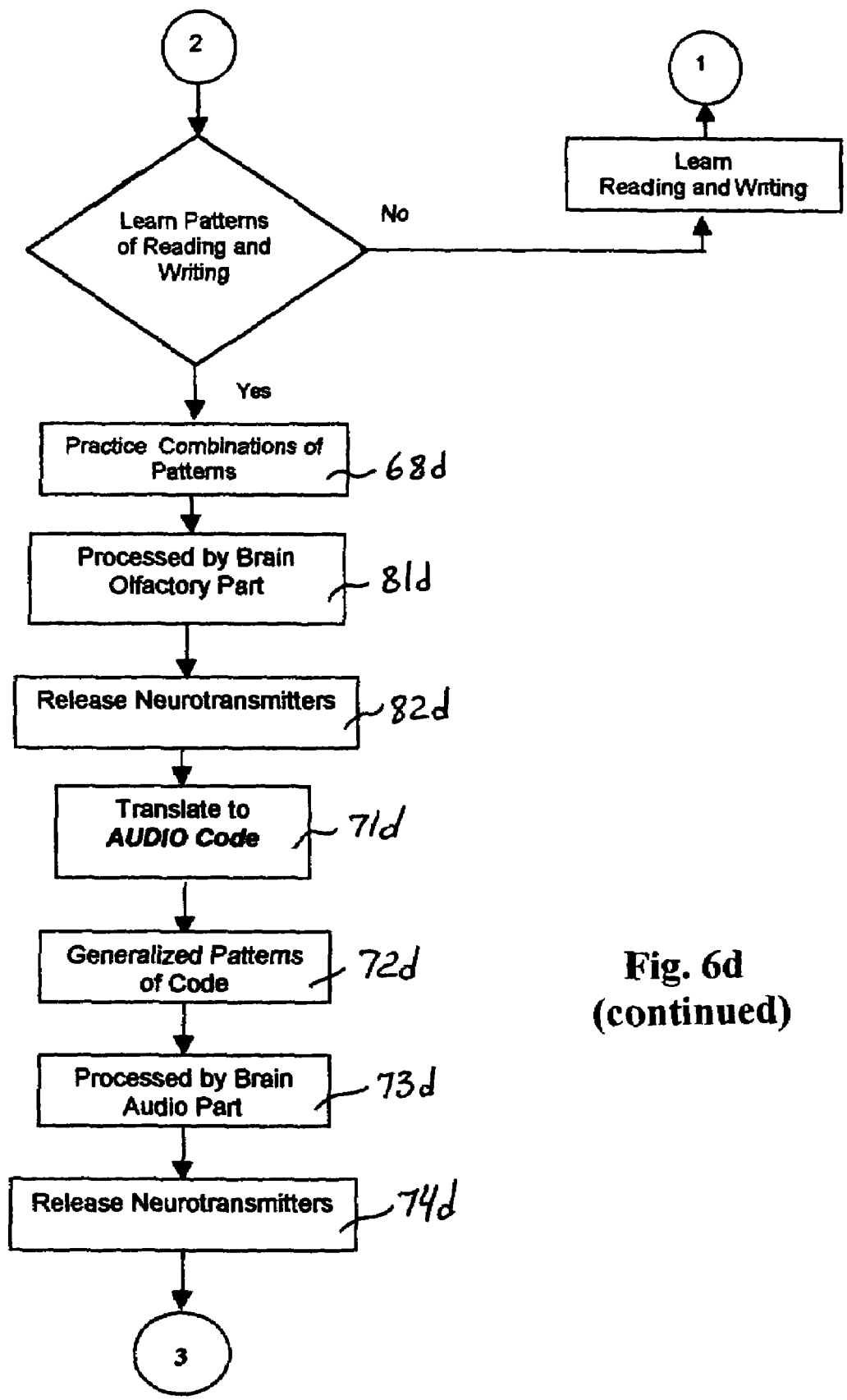
Figure 6D:
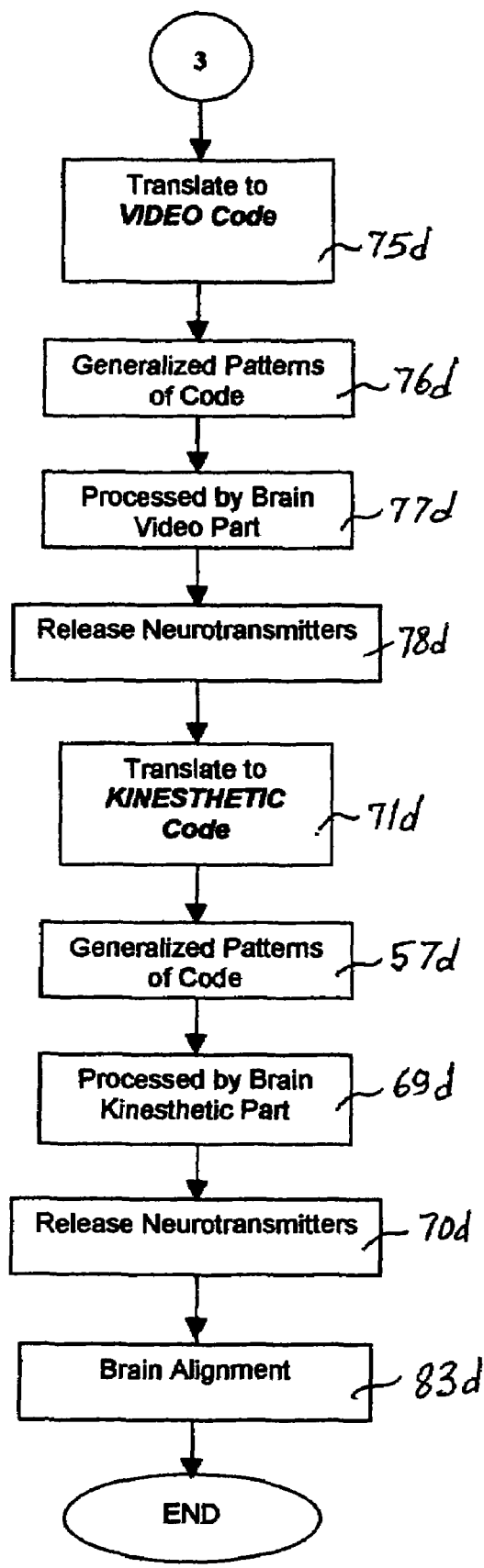

Each of the psychoconduction treatments (method) 43-45 (see FIG. 3) can be presented, for example, by either one of an audio psychoconduction code, video psychoconduction code, kinesthetic psychoconduction code, olfactory/tactile (tactile is not shown) psychoconduction code, etc. In FIG. 6a are shown the steps of the psychoconduction treatment. The operator generalizes patterns of code (block 57) for the selected appropriate either one of the mentioned above treatments. Then operator provides selection of the appropriate needed subject for improvement, e.g. such as learning improvement of addition, multiplication, subtraction, division or reading and writing (blocks 58-62). On the basis of the selected learning improvement is provided psychoconduction code and/or pattern of the selected learning subject (blocks 63-67) respectively. If non of the subjects is separately selected, the method conducts the practice of the pattern combination 68, which has to be processed by the appropriate part of the brain, e.g. for kinesthetic treatment the kinesthetic part of brain processes the patterns 69 providing the neurotransmitters release 70. The next steps of the method are to provide introduction of the audio code 71 in the analogous sequence of the steps (operations) 72-74, video code 75 in the analogous sequence of the steps (operations) 76-78, and olfactory code 79 in the analogous sequence of the steps (operations) 80-82. For audio (see FIG. 6b/blocks 57b-83b/), video (see FIG. 6c/blocks 57c-83c/) and olfactory (see FIG. 6d/blocks 57d-83d/) are used the same principles, but in the biased sequence. All described steps provide the brain alignment of the psychologically disordered object 83.

Figure 8:
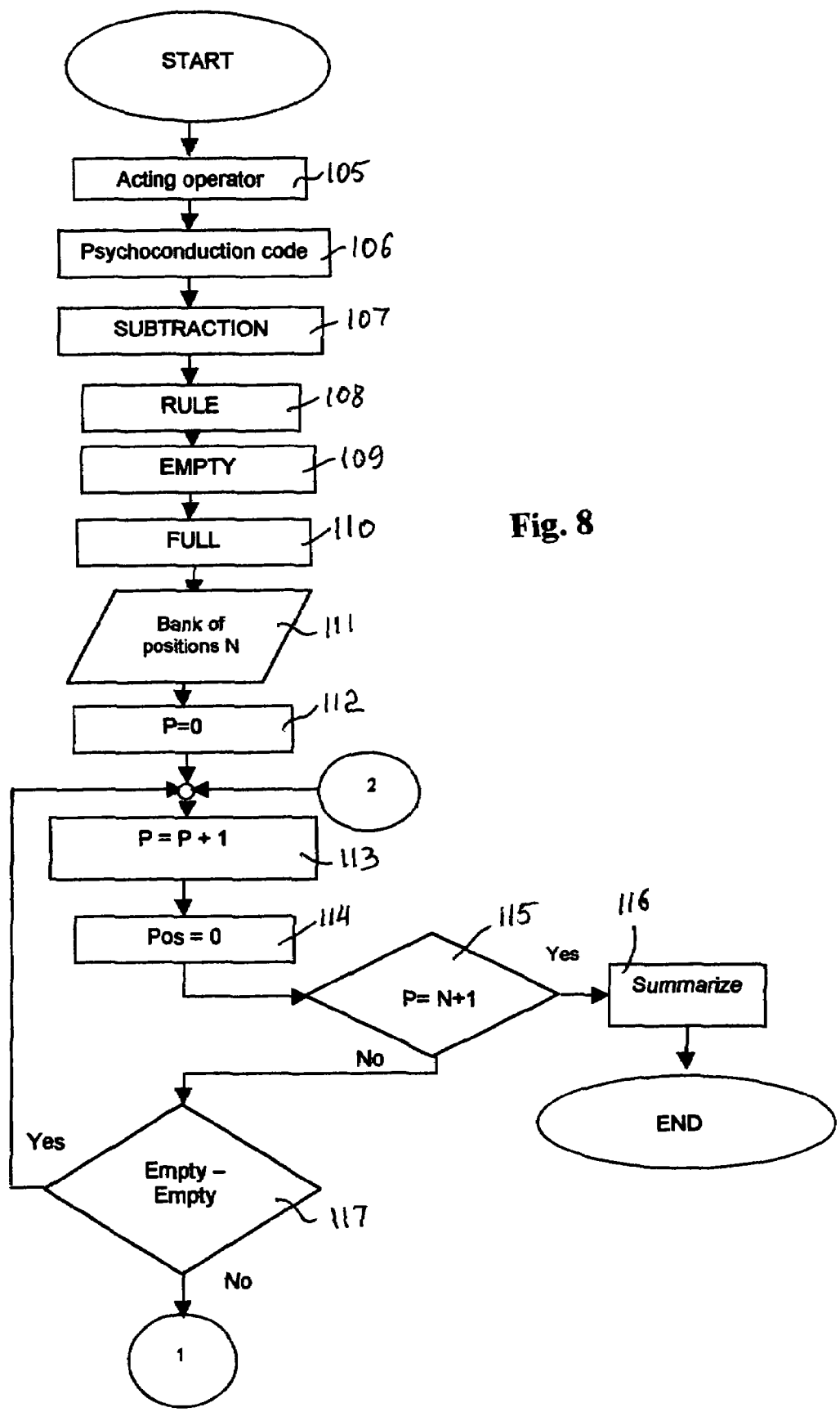
Figure 8:
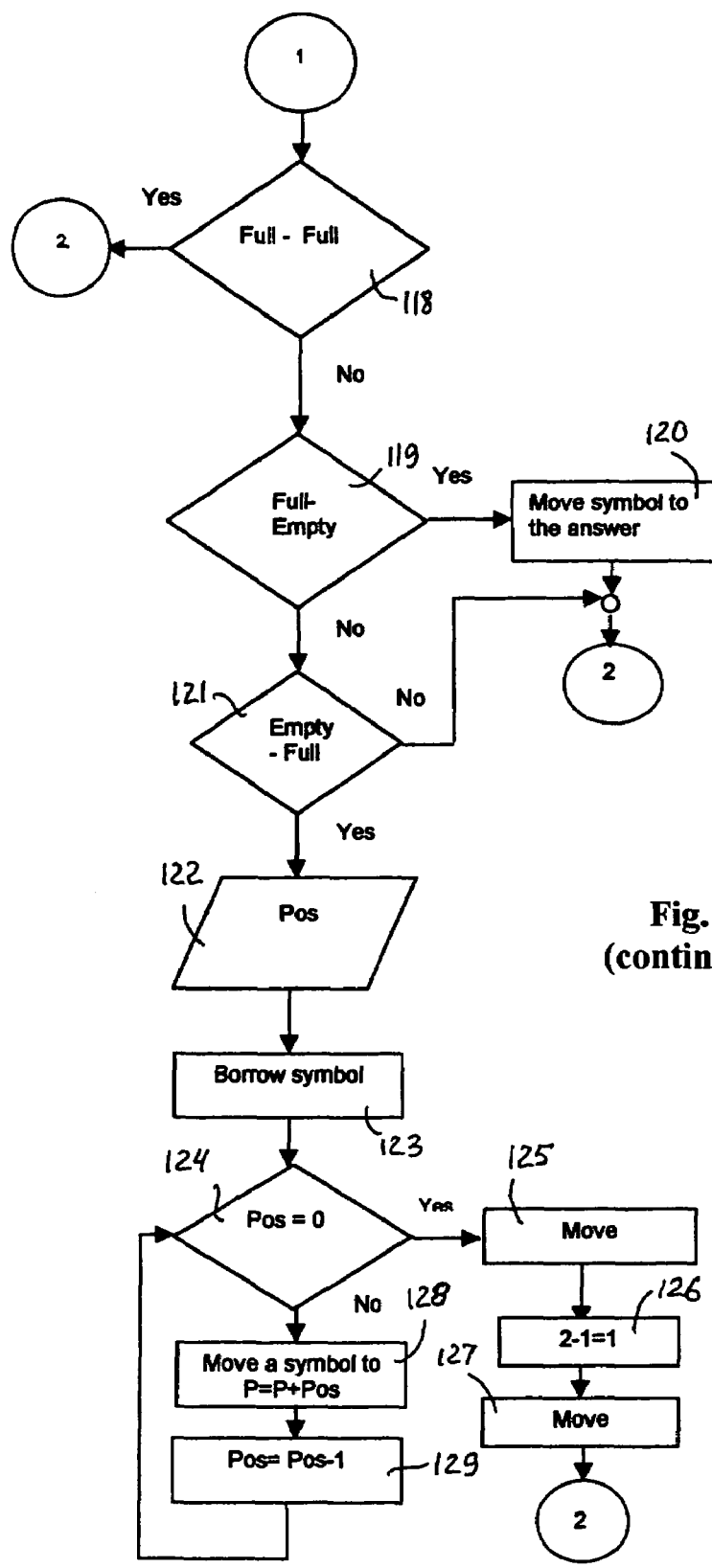
Figure 9:
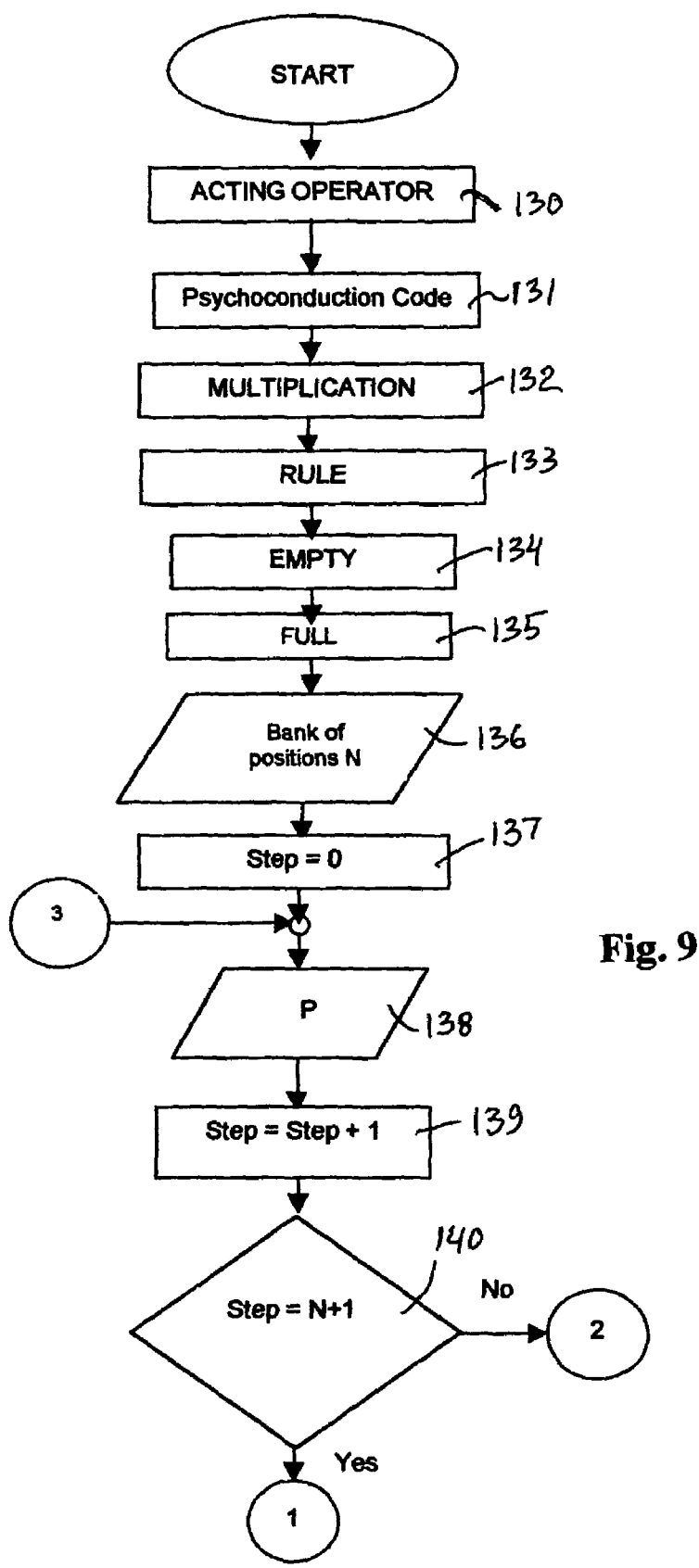
Figure 9:
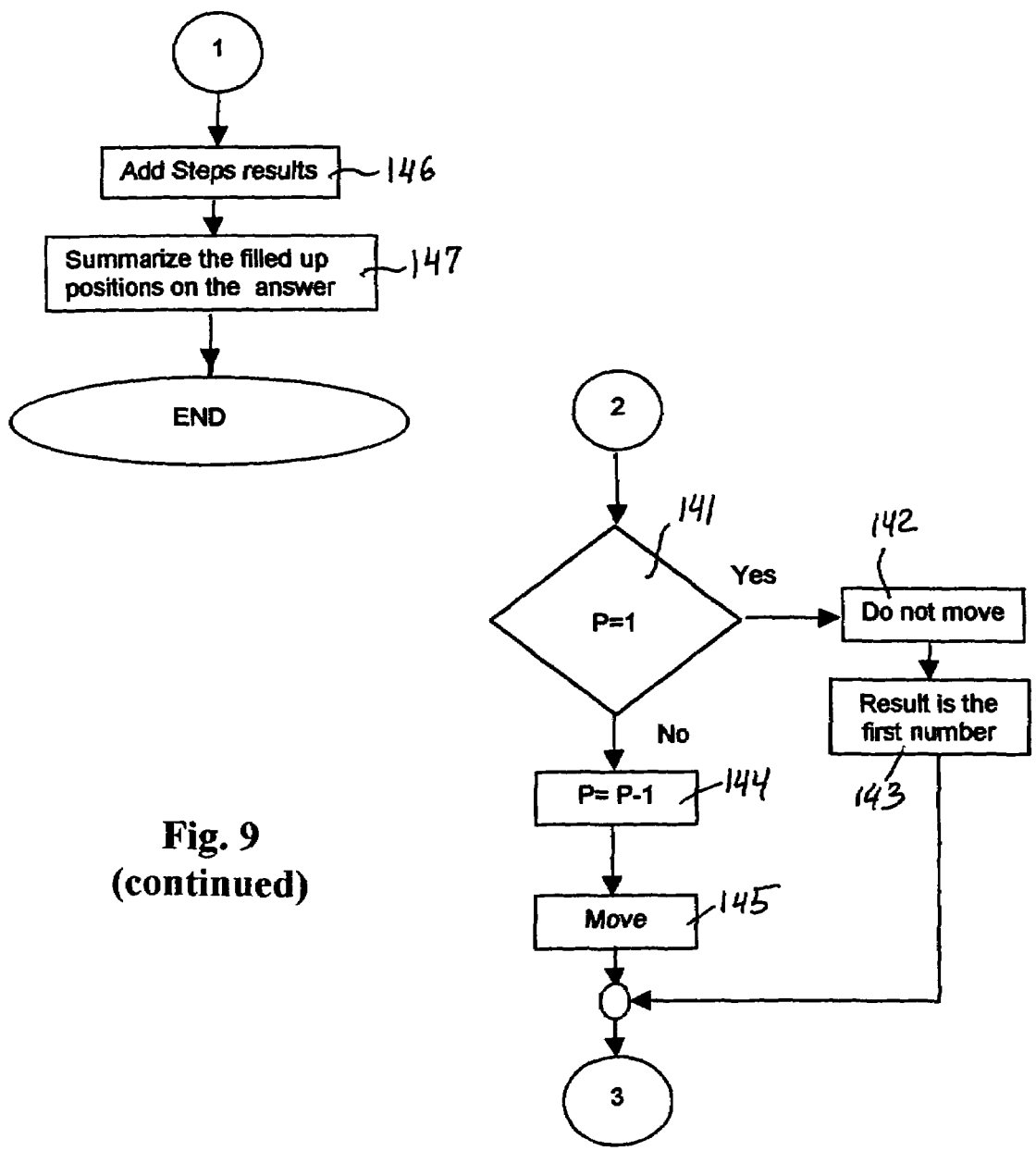
Figure 10:
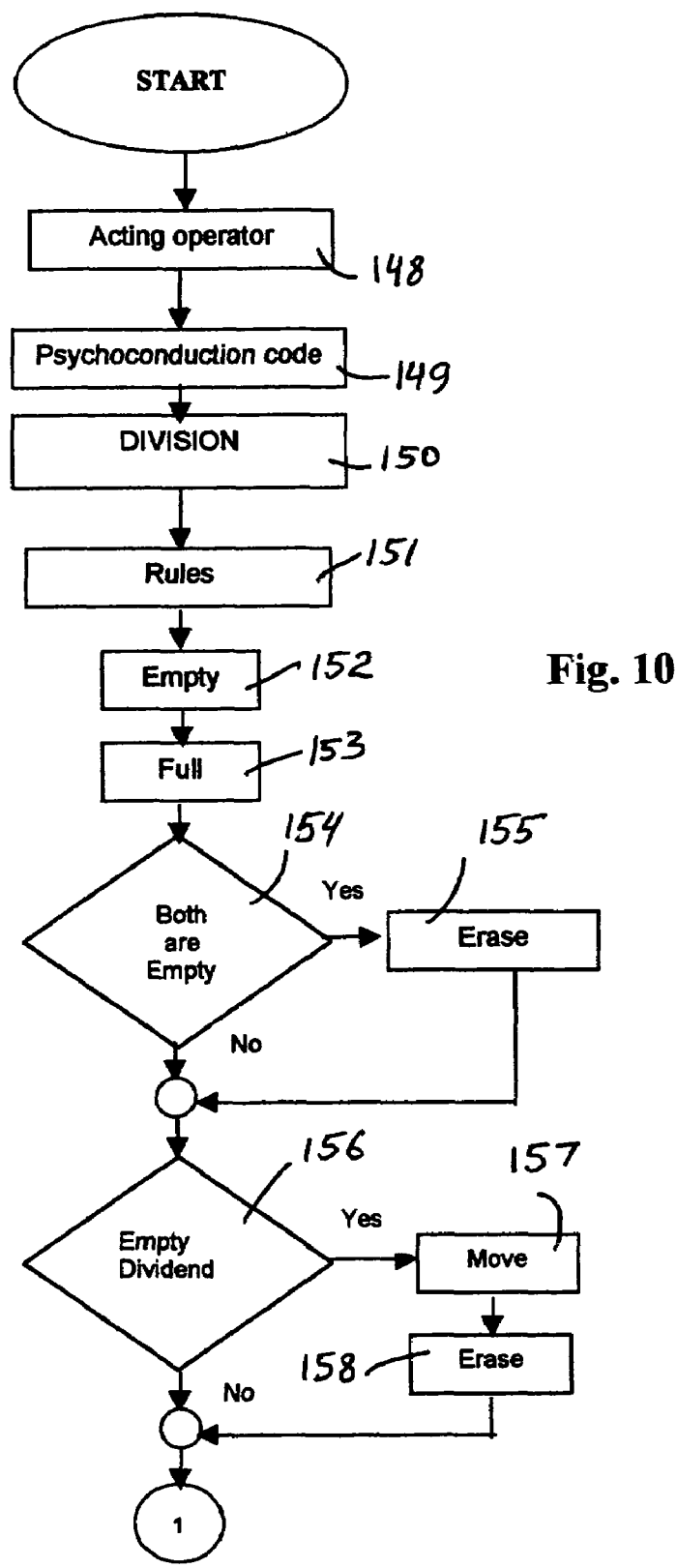
Figure 10:
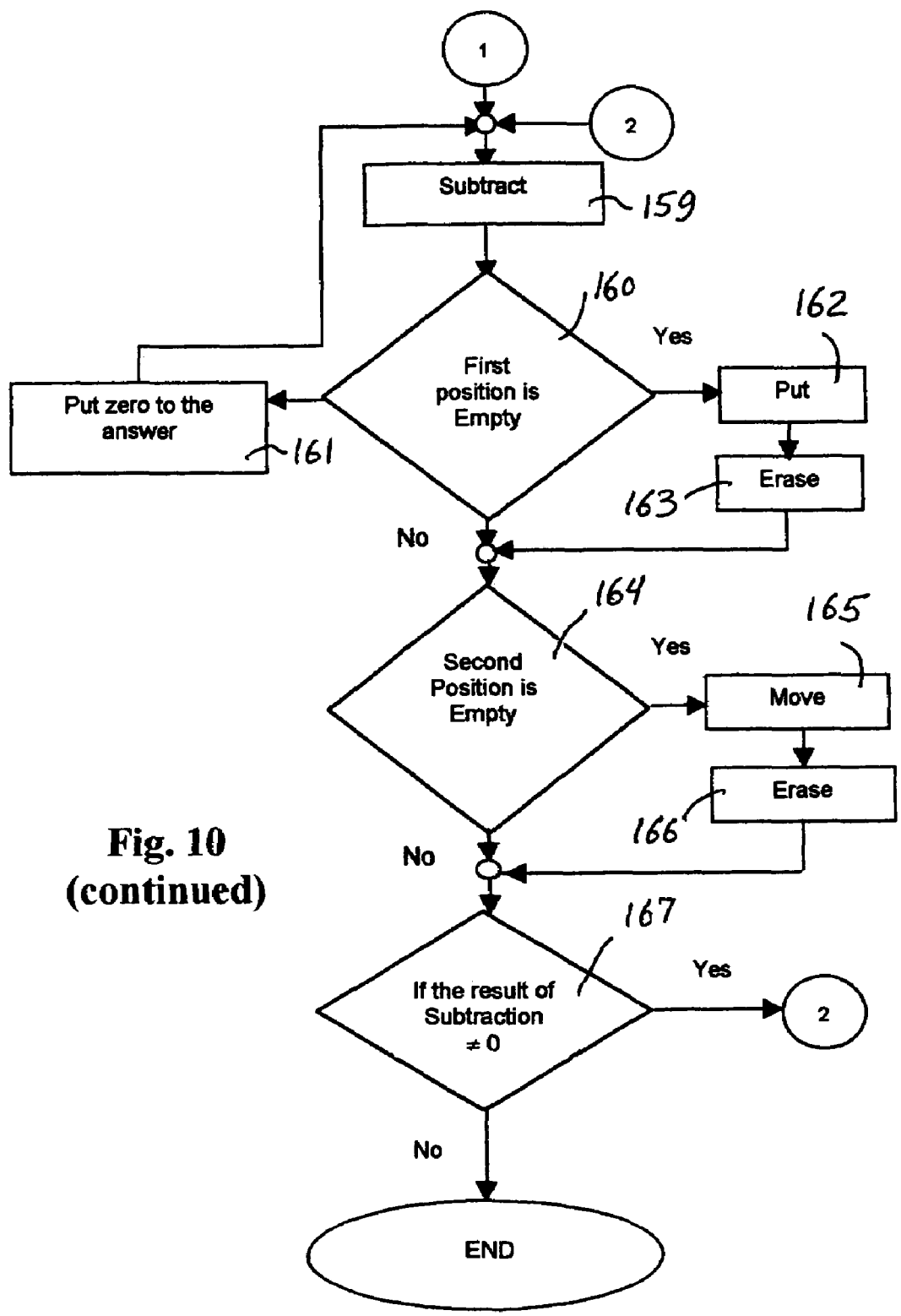

For example, for the learning process improvement, the psychoconduction method for mathematical addition can be presented by the sequence of the steps as follows in FIG. 7. The acting operator 84 (after object addition improvement has been selected 85) selects the addition rules 86 (e.g. each advanced position is twice bigger than the prior position). The bank of positions "N" is formed for each arithmetical number 87. Conditionally assume, that position without symbol is "empty" 88 and the position the symbol is "full" 89, as it has been described herein above. Assigning "P" as a current position and "E" as an advanced position to the first arithmetical number to place the symbol 90, the next step provides calculation of the current position $P_1=P+1$ (block 91) the counter for the current position is equal to. For the next step method provides a calculation of the advanced position POS=0 (block 92), and summarizing of the symbols in the current column 93, considering counter P≈N+1 for the current position 94. If P=N+1 the method provides the output of the value summary for the filled-up positions on the arithmetic result 95. After the sum 93 is input, the analysis of the non-equality of the sum to "0 (zero)" is provided 96, and the current column is "empty", then the next position is considered E=E+1 (block 97) where "E" is a counter of advanced position for the another symbol placement. If SUM=1 (block 98) and symbol "1" in the column (parallel position) 99 then P+POS and the iteration is provided. In the case when SUM≈1, the current position is changed to POS=POS+1 (block 100) and the number of symbols is checked for the even condition SUM=Even (block 101). If the equation in block 101 is correct, the division SUM=SUM/2 (block 102 is provided for the even number of the symbols at the same column (parallel position). For the odd number of symbols (SUM≠Even/SUM=Odd/), the "1" is subtracted from the sum of symbols at first column (block 103) and the symbol is changed (block 104) for the sequential iteration. For the psychoconduction of the learning improvement in subtraction, multiplication and division are used the principles based on equation [1] and on the analogous principles assumptions described of the above. The flow chart for subtraction (blocks 105-129) is shown in FIG. 8, the flow chart for multiplication (blocks 130-147) is shown in FIG. 9, and the flow chart for division (blocks 148-167) is shown in FIG. 10.

Figure 11:
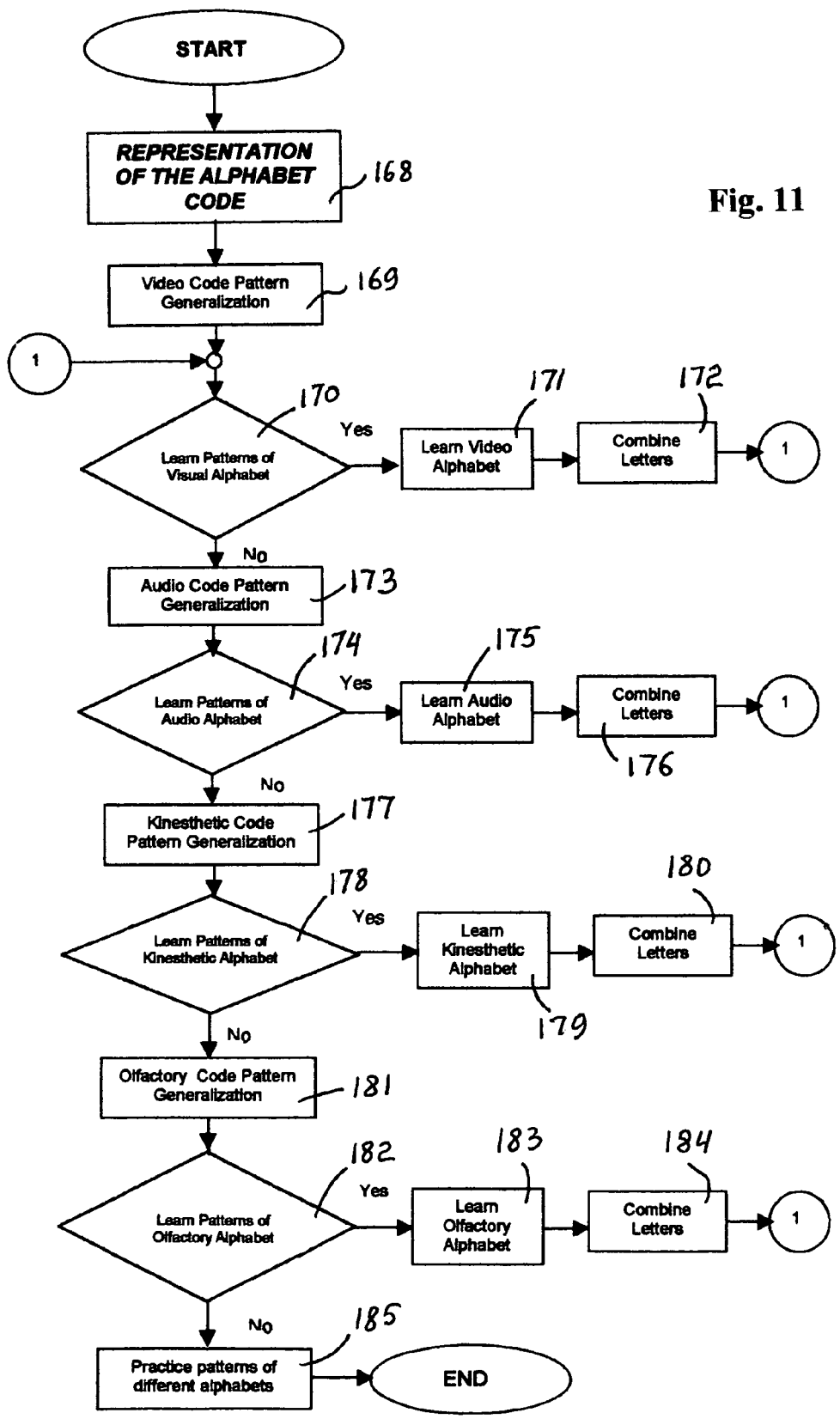
FIGS. 11, 12a, 12b are the flow charts illustrating the methods for brain stimulation of the psychologically disordered object during letter(s)/word(s) writing, reading learning improvement.

The general steps for the reading/writing learning improvements of the psychologically disordered object the psychoconduction method includes the following steps as shown in FIG. 11. After the psychoconduction code (codogram) is selected 168, the video code pattern is generalized 169, if initially the pattern of learning of the alphabet is selected as a visual treatment 170. The video pattern of the alphabet in the psychoconduction code 171 and combination of the letters 172 is studied by the object (object reads/writes the letters under influence of codograms). If the visual object's perception of the letters is not satisfied, the pattern is generalized into sonic pattern of the alphabet 173 and the object's alphabet study 174 is provided in the codogram sonic influence of the letters 175 and their combinations 176 respectively. When the operator (acting operator) is not satisfied with the object's learning results for the alphabet audio representation, the learning process is conducted in compliance with the kinesthetic treatment (blocks 177-180) or olfactory treatment (blocks 181-184). The operator provides evaluation of the object's achievements and can assign the combined treatment 185 comprising different codograms representation (e.g. for some letters or words/sentences can be used the sonic treatment, but for other letters of the alphabet can for instance be used the kinesthetic treatment).

The psychoconduction code for reading/writing improvement of the psychologically disordered object on the basis of the audio, video, kinesthetic and/or olfactory treatment can be tabulated and shown in the Table 1 (in the Table 1 is conditionally shown the psychoconduction code combinations/ codograms/ for English language as an example, but the codograms can be presented for any known language). The steps of psychoconduction code combination creation for each letter of alphabet is shown in FIGS. 12a, 12b for writing and reading respectively.

Figure 12A:
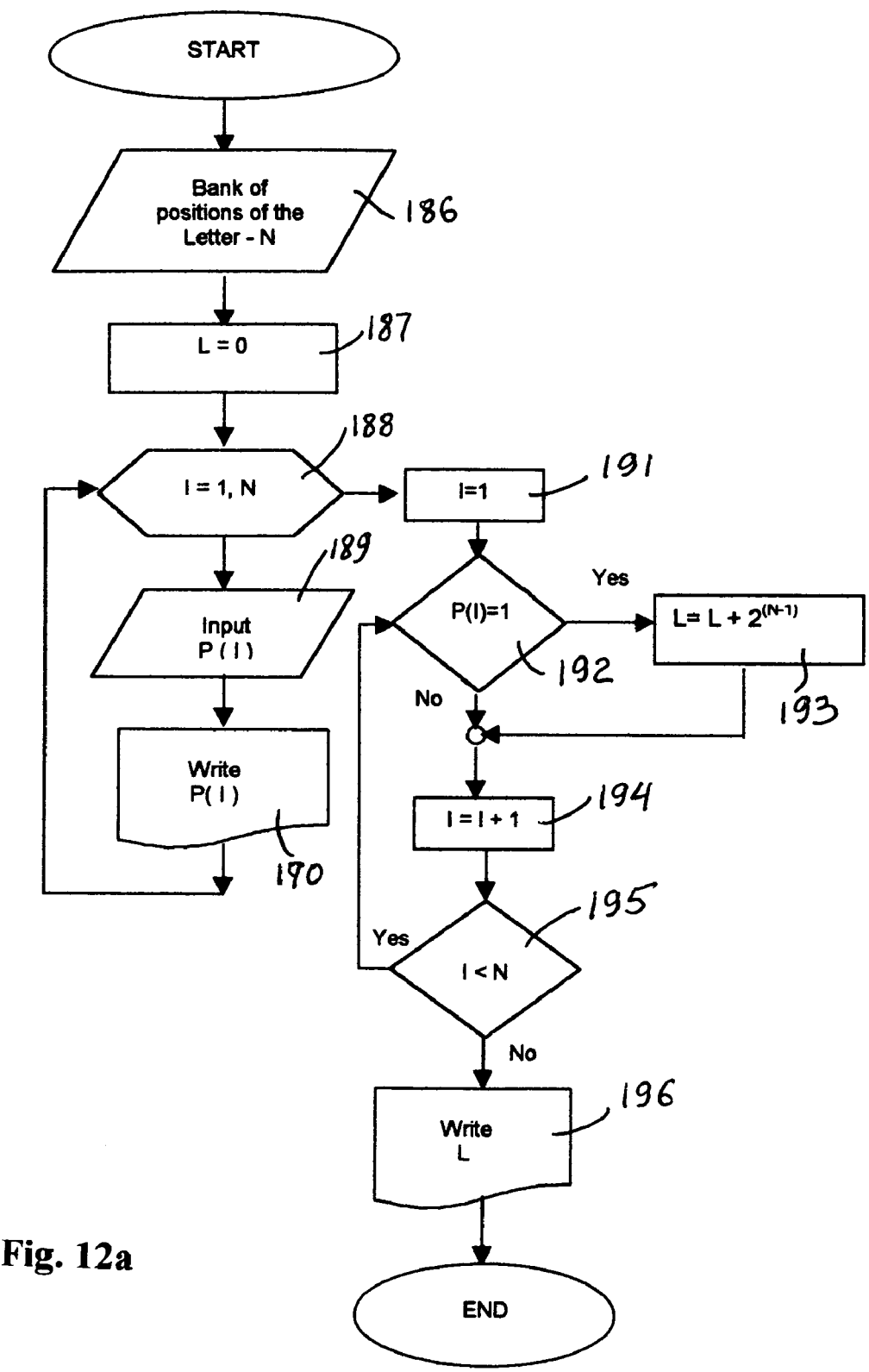
Figure 12B:
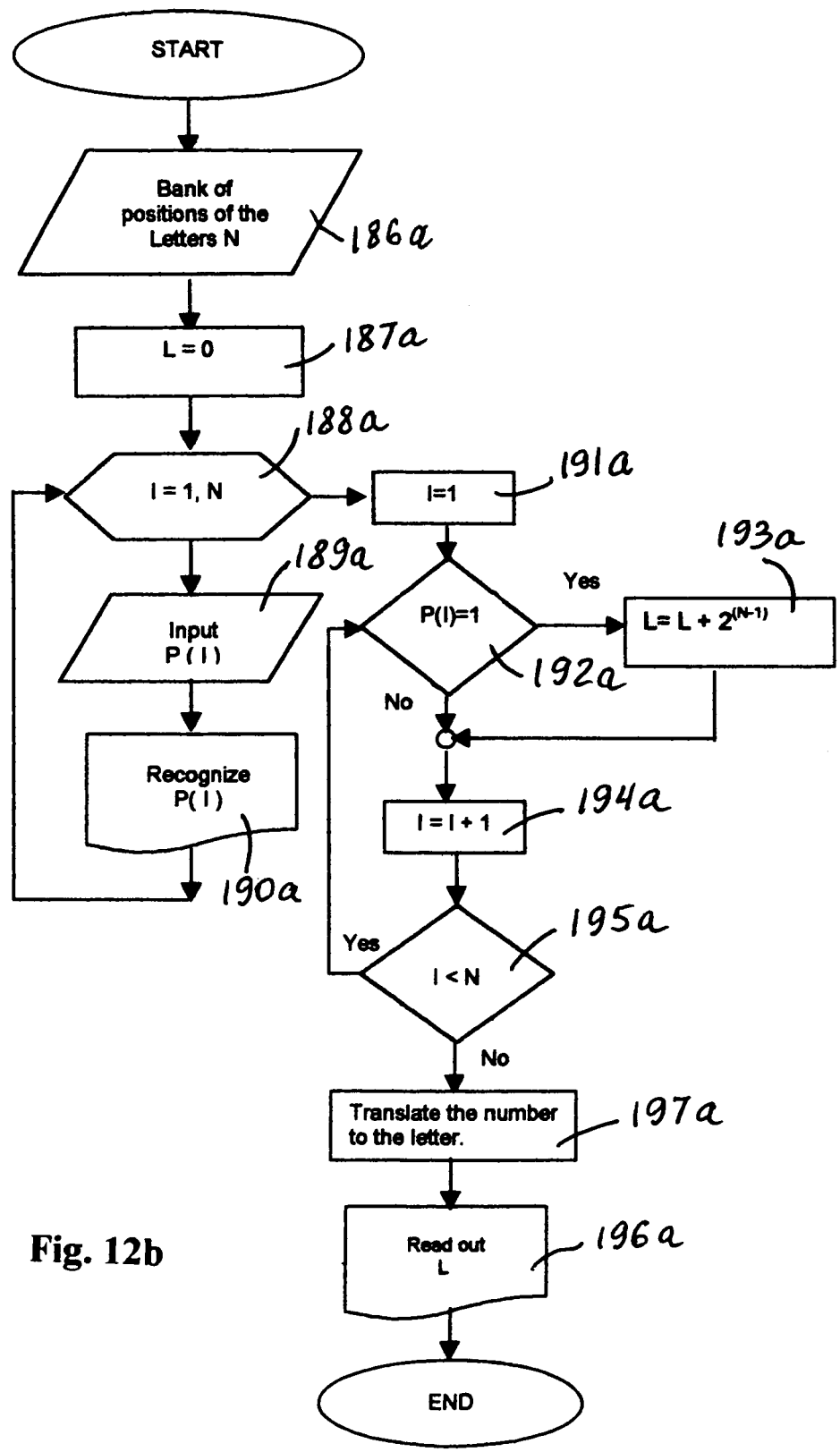

Referring to FIG. 12a, after the bank of the letters' positions is formed 186, the appropriate number for each letter of the alphabet is assigned 187 according to the selected psychoconduction code (e.g. in compliance with [1]). As shown in the block 187, it conditionally is assumed that the first letter of the alphabet is equivalent to the "0 (zero)". The method provides iteration (cycle) specific number assignment for each letter in sequence according to the steps 188-196 (see also the Table 1). The FIG. 12b illustrates the steps (blocks 186a-197a) for reading learning improvement, and the process of the reading learning is similar to the writing learning shown in FIG. 12a.

TABLE 1

| 1  | A |   |   |   |   | x | Or |   |   |   | 0 | x |
|----|---|---|---|---|---|---|----|---|---|---|---|---|
| 2  | B |   |   |   | x |   | Or |   |   | x | 0 |   |
| 3  | C |   |   |   | x | x | Or |   |   |   | x | x |
| 4  | D |   |   | x |   |   | Or |   | x | 0 | 0 |   |
| 5  | E |   |   | x |   | x | Or |   | x | 0 | x |   |
| 6  | F |   |   | x | x |   | Or |   | x | x | 0 |   |
| 7  | G |   |   | x | x | x | Or |   | x | x | x |   |
| 8  | H | x |   |   |   |   | Or | x | 0 | 0 | 0 |   |
| 9  | I | x |   |   |   | x | Or | x | 0 | 0 | x |   |
| 10 | J | x |   |   | x |   | Or | x | 0 | x | 0 |   |
| 11 | K | x |   |   | x | x | Or | x | 0 | x | x |   |
| 12 | L | x |   | x |   |   | Or | x | x | 0 | 0 |   |
| 13 | M | x |   | x |   | x | Or | x | x | 0 | x |   |
| 14 | N | x |   | x | x |   | Or | x | x | x | 0 |   |
| 15 | O | x |   | x | x | x | Or | x | x | x | x |   |
| 16 | P | x |   |   |   |   | Or | x | 0 | 0 | 0 | 0 |

TABLE 1-continued

| 17 | Q | x |   |   | x | Or | x | 0 | 0 | 0 | x |
|----|---|---|---|---|---|----|---|---|---|---|---|
| 18 | R | x |   | x |   | Or | x | 0 | 0 | x | 0 |
| 19 | S | x |   | x | x | Or | x | 0 | 0 | x | x |
| 20 | T | x | x |   |   | Or | x | 0 | x | 0 | 0 |
| 21 | U | x |   | x |   | x  | Or | x | 0 | x | 0 | x |
| 22 | V | x |   | x | x |    | Or | x | 0 | x | x | 0 |
| 23 | W | x |   | x | x | x  | Or | x | 0 | x | x | x |
| 24 | X | x | x |   |   |    | Or | x | x | 0 | 0 | 0 |
| 25 | Y | x | x |   |   | x  | Or | x | x | 0 | 0 | x |
| 26 | Z | x | x |   | x |    | Or | x | x | 0 | x | 0 |

The operator 10 by, for example, a control means 9 (or by any other terminal means 6, 7 or 8) of the terminal means 5 selects the initial treatment (e.g. audio treatment or any one).

Psychoconduction consists the four different parts. The first part is the calibration of the brain, with the opportunity to increase the brain's intellectual capacity. This approach deals with the training of the brain to achieve congruency in responses on visual, audio, kinesthetic, and olfactory stimuli. The brain needs to be exposed to different pattern of stimuli without explanation or the logical connection in the patterns design. The second part of the method provides the changes in the structure of the brain cells and allows the non-functional cells to be replaced by others, which are able to function in desired capacity. The third part includes the therapy, that reduces the discrepancies in the perceived and real emotional experiences and increases the equilibrium of the emotional experiences. The fourth part of psychoconduction is as mentioned above called the psychoconduction code (codogram or Litvin's code) and provides the unlimited amount of the patterns to balance and restructure the brain cells. The codogram can be for example based, as it is mentioned above, on binary arithmetic and provides the easy absorption by brain and is easily translated into audio, visual, kinesthetic and olfactory stimuli.

Psychoconduction creates the congruence between different modes of communication, which are the sonic, visual, kinesthetic and olfactory, and provides the training for the different parts of the brain in order to release the congruent amount of chemicals in reaction on the sonic, visual, kinesthetic and olfactory stimuli. The psychoconduction training provides the use of the coded patterns and translation of them to the different stimuli. In this stage of the treatment the psychologically disordered object only intuitively understands the patterns, which are clear in the next stage of treatment. The complication of the patterns is increased from the stage to stage. The psychoconduction method translates the patterns from the one of the modes of expression to the other. The recognition and processing of the same information transmitted in the audio, video, kinesthetic and olfactory form provide the calibration of the different parts of the brains. The purpose of the improved training/treatment is to achieve the congruence of the different parts of the brain response on the same patterns, but in the different forms of representation. In compliance with FIGS. 3-6, the patterns provided by the psychoconduction code that are the combinations of positions, which are represented, for instance, by the symbols conditionally called as "full" or "empty". Such symbols are represented in video, audio, kinesthetic and/or olfactory stimuli (the patterns are translated from the one representation to the another).

Figure 13:
FIGS. 13-18 are the simplified representation of the psychoconduction coded combinations visual representation.

For example, in FIG. 13 is presented the video pattern (visual information) of some learning symbol (e.g. letter) for the visual treatment of the psychologically disordered object using the method shown in FIG. 6 applied for the video codogram. Assume, that the audio treatment is needed to be conducted at the next stage of the psychological treatment. The psychoconduction method provides the translation (transformation) of the visual information (e.g. visual information presented in FIG. 13) by the controller 3 in the sonic information, for instance, such as "sound (e.g. knock)—sound (e.g. knock)—double sound (e.g. double knock)". Such video and audio codograms balance the visual and sonic reaction of the psychologically disordered object on the symbolic picture on the displaying means 11 and the sound combination from the audio means 12. Each "single sound" represents a filled up ("full") position and "double sound" represents an "empty" position, as it is shown in FIG. 13. As it was mentioned above, the symbolic "full" ("1", "x", etc.) and "empty" ("0", "o", etc.) in the present disclosure will be used hereinafter in the text of the disclosure, and the "dot" in the rectangle will represent the meaning "full" and empty rectangular (no dot) will represent the meaning "empty" in the illustrations shown in FIG. 13 and further in the FIGS. 14-18.

For kinesthetic representation of the sonic perception, for example, the clamping of the right hand can represent a "single sound" and the tightening of the left hand into a fist can represent a "double sound", or the clamping of the right hand then represents "full" position and clamping of the left hand represents "empty" position. For this example, the kinesthetic representation of the combination "empty-full" is to clamp the left hand once then the right hand once. The another kinesthetic treatment can be provided with the auxiliary equipment 14 (e.g. with the stepping board). The kinesthetic representation for the board with four sides is, for instance, the stepping on one side to show that the first position is "x". The object moves to another side of the board and steps on the board again to show that the second position is "x" too. Eventually, the moves to the third side of the board without stepping on the board show that third position is "o".

Figure 7:
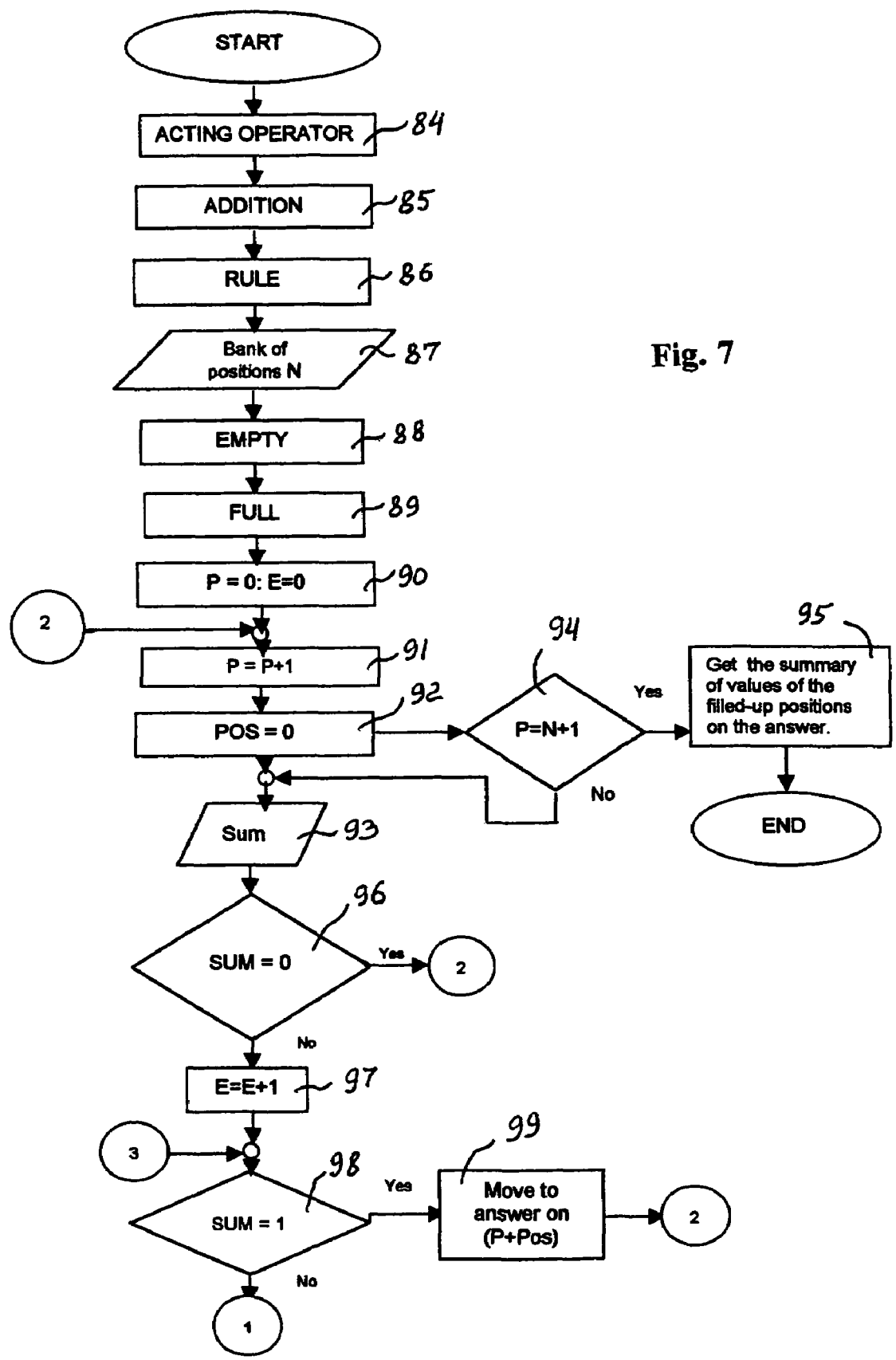
FIGS. 7-10 are the flow charts illustrating the methods for brain stimulation of the psychologically disordered object during mathematical addition, subtraction, multiplication and division learning improvement respectively.
Figure 7:
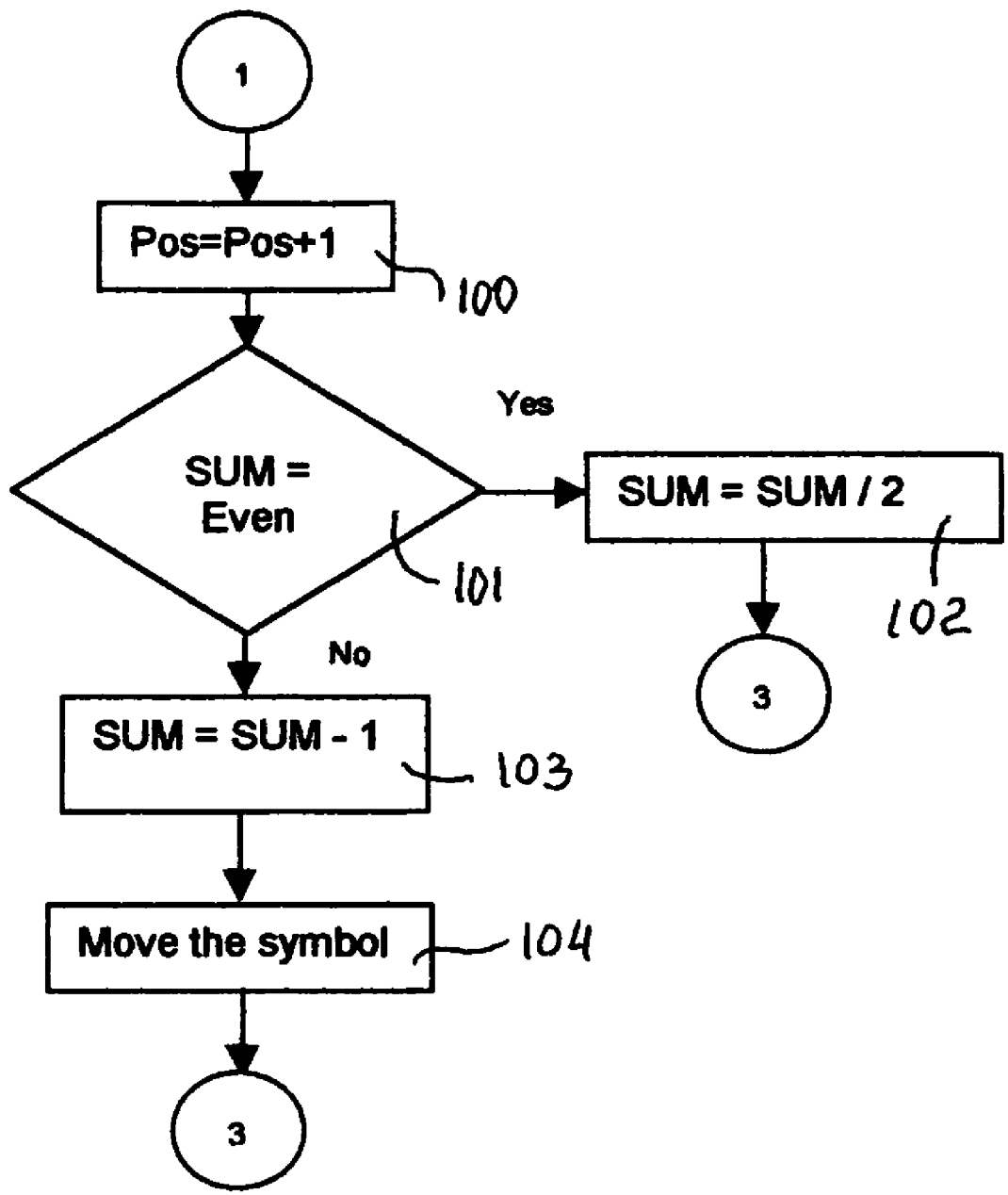
Figure 14:
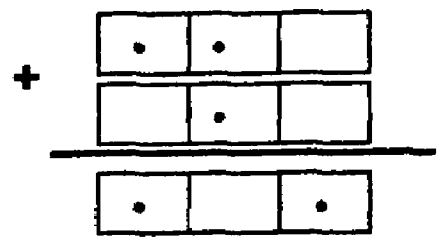

In FIG. 14 is shown the example of the arithmetical addition (e.g. 3+2=5) learning improvement treatment according FIG. 7. This example illustrates the higher level of the different parts of the brain balance on the same patterns using the different modes of communication. The audio representation, according FIG. 6 for audio treatment, of the picture in FIG. 14 is "knock—knock—double knock—different sound (e.g. tram)—double knock—knock—double knock—different sound (e.g. cling)—knock—double knock—knock".

The brain balance is provided by the visual and sonic reaction using the visual symbols "x", "o" and sonic symbols "knock, double knock, tram, and cling". The sound "knock" represents a "x" position, double knock represents "o" position, tram represent visual sign plus ("+"), and cling represents visual sign equal ("="). Kinesthetic representation (FIG. 6 for kinesthetic treatment) can be for knock is clamping of the right hand, double knock is tightening the left hand into a fist, tram is extended left hand, and cling is the crossed two hands. Clamping of the right hand represents the "x" position, the left hand clamping represents "o" position, and extending one hand represents sign plus, crossed both hands represent sign equal. For the four-sides board the psychologically disordered object moves, for instance, around the board stepping on one side to show that the first position is "x". Moving to the another side and stepping on the board the object shows that the second position is "x" too. When the object located at the third side of the board without stepping on the board to show that the third position is "o", etc.

Figure 15:
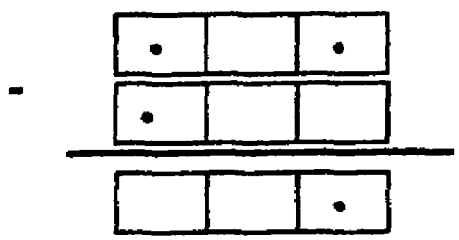

In FIG. 15 is shown the example of the arithmetical subtraction (e.g. 5–1=4) learning improvement treatment in compliance with FIG. 8. The audio representation of the FIG.

15 is "knock—double knock—knock—double tram—knock—double knock—double knock—cling—double knock—double knock—knock". The double tram represents sign minus ("−"). The kinesthetic representation of the double tram can for example be both hands extended forward. The kinesthetic representation for hands movement is: right, left, right, both extended forward, right, left, left, both crossed, left, left and right. The kinesthetic representation for the movements around the board is: step on, without step, step on, extend both hands forward, step on, without step, without step, cross both hands, without step, without step, and step on.

Figure 16:
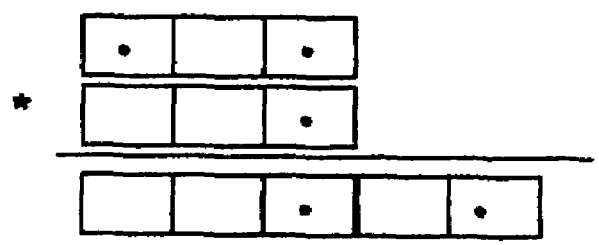

The arithmetical multiplication (e.g. 5×4=20) learning improvement of the psychologically disordered object by psychoconduction code for video treatment shown in FIG. 9 is graphically illustrated in FIG. 16. The audio representation of the FIG. 16 is "knock—double knock—knock—blick—double knock—double knock—knock—cling—double knock—double knock—knock double nock—knock". The blick ("*") represents visual sign of multiplication. The kinesthetic representation of the blick can, for example, be the one hand extended up. The kinesthetic representation for hands movement is: right, left, right, one hand extended up, left, left, right, both crossed, left, left, right, left and right. Kinesthetic representation for the movements around the board can be: step on, without step, step on, extend one hand up, without step on, without step, step on, cross both hands, without step, without step, step on, without step, step on.

Figure 17:
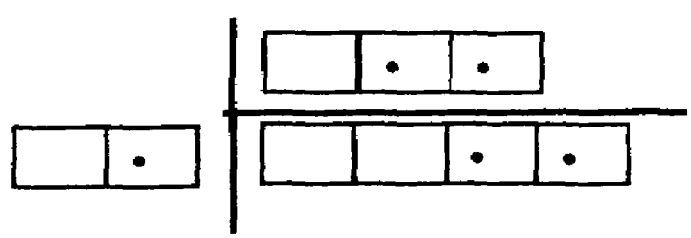

The FIG. 17 illustrates the arithmetical division (e.g. 12:6=2) learning improvement treatment by the method shown in FIG. 10. The visual presentation of the FIG. 17 can be translated by the psychoconduction code in the sonic perception of the division operation, as "double knock—double knock—knock—knock—double click—double knock—knock—cling—double knock—knock—knock. The double blick represents division sign. The kinesthetic representation of the double blick can be the both hands extended up. The kinesthetic representation for hands movement can be: left, left, right, both hands extended up, left, right, both crossed, left, right, and right. Kinesthetic representation for the movements around the board can be: without step, without step, step on, step on, extending both hands up, without step, step on, cross both hands, without step, step on, and step on.

Figure 18:
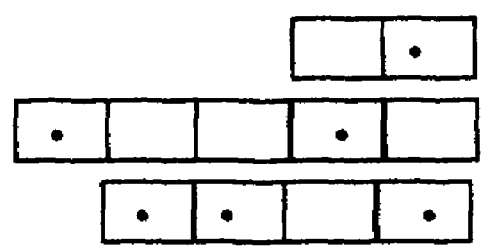

The FIG. 18 represents the visual codogram for letter(s)/word(s) reading/writing (e.g. the word "ARM") treatment illustrated in FIGS. 11, 12. The visual codogram presented in FIG. 18 can be translated (transformed) in the sonic codogram as "knock—double knock—chick—double knock—knock—double knock—double knock—knock—chick—knock—double knock—knock—knock". The chick represents sign of space between letters. The kinesthetic representation of the chick can be the one of the hands shaking. The kinesthetic representation for hands movement is: right, left, left, left, one of hands shaking, left, right, left, left, right, one hand shaking, right, left, right, and right. Kinesthetic representation for the movements around the board can be: step on, without step, without step, without step, shaking one hand, without step, step on, without step, without step, step on, shaking one of the hands, step on, without step, step on, and step on.

The steps of the methods, illustrated in FIGS. 3-12, and the banks of the positions are memorized in the memory 4. By the command(s) from, for example, the control panel 9 of the terminal means 5 the controller provides the indication of the video information on the displaying means 11 or via audio means 12 depending on the selected treatment (audio or video).

If the kinesthetic or olfactory treatment is selected by operator 10, the auxiliary equipment 14 (e.g. such as step board, fragrant, etc.) can be provided by the operator 10 for the psychologically disordered object 13.

According structurization of the brain cells, the psychoconduction method provides the "work" with the primitive stem cells in genetics (see FIG. 3, block 17). The stem cells could be transferred to the different functional cells. The psychoconduction code provides assistance of the simple brain cells for the complex information processing, and the simple cells 17 are functioning as the complex cells 18. Commonly, the simple brain cells respond to the stationary stimuli, such as lines, bars, and edges, whereas the complex cell responds to more complex stimuli and more sophisticated forms. The difficulty of the brain to process complex information is mainly attributed to difficulty of complex cells to process complex information due to physiological issues receiving incomplete or distorted request or the limitation of the capacities of the complex cell. The main purpose of the codogram in processing of the information by brain cells is to clear request with the not distorted data to process an acquired information and find the right address for requested information. Psychoconduction is simplifying the request to process information, and, by modifying the simple cells for processing the stimuli of the same information as the complex cells do.

The codogram creates the new functional cells, that process and congruence the complex information in the response to the sonic (audio), visual (video), kinesthetic and/or olfactory stimuli of the psychotherapy by the improved psychoconduction method (codogram).

The psychoconduction code provides the better (more effective) activity of simple cells by using simple stimuli in complex patterns to substitute the use of injured or underdeveloped complex brain cells. The improved method uses the simple cells, which are responsible for processing the simple stimulus. Psychoconduction enhances the process of information, stimulating the brain with the simple symbols and transferring them between the different areas of the brain. These transfers are between the areas responsible for different functions: audio to the visual, audio to kinesthetic, visual to audio, visual to kinesthetic, kinesthetic to visual, kinesthetic to audio. For instance, the olfactory functions can be used for the brain information processing. Benefits of processing the simple stimuli in the different brain areas are in creating additional axons for the impulse traveling, and by enhancing the brain capacity for complex patterns of simple symbols processing. The same pattern of the simple symbol translated by the brain to the different expression creates the internal communication and enhancing the brain's equilibrium. By using a different part of the brain to process the same pattern, codogram compensates the inadequate information and assists the object to avoid psychological difficulties. The brain also provides the clarity of the logical patterns of the simple symbol and opportunity for all different parts of the brain to enhance performance using the congruent responses presented to the object in the psychoconduction code utilizing the complex pattern in the form of the simple visual, sonic, kinesthetic, olfactory, tactual (not shown), etc. symbols. It is important, for the object with the difficulties, for example, in processing of the visual information to process visual symbols as the last and other symbols before to have valid references. In this case, the psychoconduction method provides the object with adequate audio or kinesthetic codogram 20 that object can translate it to the visual symbol.

CONCLUSION, RAMIFICATION AND SCOPE

Accordingly the reader will see that, according to the invention, I have provided the improved method and system for psychological treatment by brain stimulation of the psychologically disordered object. The improved method and system have various possibilities, considering variety of the psychologically disordered object possible improvements.

While the above description contains many specificities, these should be not construed as limitations on the scope of the invention, but as exemplification of the presently-preferred embodiments thereof. Many other ramifications are possible within the teaching to the invention. For example, in the present time society is more aware that illiteracy or inadequate academic performance is not only caused by social disadvantages. As well known, it is also caused by the neuropsychological barriers. Those barriers are creating the difficulties to recognize or learn complex patterns needed to be read or to do mathematical calculations, etc. The improved method is not limited only by the described audio, video, kinesthetic, olfactory or tactual psychoconduction codes, and, for instance, the musical principles based on the piano keys (musical note alphabet from "A" through "G" in compliance with the psychoconduction codogram/not shown/), etc. can be successfully used too. The improved method and system stimulates the simple cells to assist the complex cells, and/or replace them in order to correctly perform the assigned command. For example, the same way as Braille's alphabet helps people with the visual impairments, the psychoconduction assists people with brain deficiencies. If one of testing results (by either one or combination of a visual treatment, an audio treatment, a kinesthetic treatment, an olfactory treatment, tactual treatment, and a musical treatment) reveals a partial damage of the complex cell of the brain, the improved treatment (method) provides a correction (calibration, balancing, alignment, stimulation) of an appropriate complex cell of the brain by an appropriate simple cell, or provides the correction of an address of the complex cell of the brain by an assistance of the simple cell to process the submitted stimuli. If one of testing results (by either one or combination of a visual treatment, an audio treatment, a kinesthetic treatment, an olfactory treatment, tactual treatment, and a musical treatment) reveals a complete damage of the complex cell of the brain, the improved treatment (method) provides the replacement of an appropriate complex cell of the brain by an appropriate simple cell. The improved method increases the disordered object brain capability and efficiency to perform at least the standard intellectual operations.

Thus, the scope of the invention should be determined by the appended claims and their legal equivalents, and not by examples given.

What is claimed is:

1. A method for psychological treatment for brain stimulation of a psychologically disordered object comprising the steps of:
   creating a psychoconduction code using a simple stimuli;
   creating a video pattern of a video information using said psychoconduction code;
   providing a visual test on the basis of said video pattern of said video information;
   creating an audio pattern of an audio information using said psychoconduction code;
   providing a sonic test on the basis of said audio pattern of said audio information;
   creating a kinesthetic pattern of said audio information or said video information using said psychoconduction code;
   providing a kinesthetic test on the basis of said kinesthetic pattern of said audio information or said video information;
   creating an olfactory pattern of said audio information or said video information using said psychoconduction code;
   providing an olfactory test on the basis of said olfactory pattern of said audio information or said video information;
   creating a tactual pattern of said audio information or said video information using said psychoconduction code;
   providing a tactual test on the basis of said tactual pattern of said audio information or said video information;
   creating a musical pattern of said audio information or said video information using said psychoconduction code;
   providing a musical test on the basis of said musical pattern of said audio information or said video information;
   providing at least one or combination of a visual treatment, an audio treatment, a kinesthetic treatment, an olfactory treatment, a tactual treatment, a musical treatment for an appropriate complex cell correction by an appropriate simple cell of said brain, and wherein said at least one or said combination of the treatments for said brain is provided to treat a partial damage of said complex cell of said brain;
   providing said at least one or said combination of said visual treatment, said audio treatment, said kinesthetic treatment, said olfactory treatment, said tactual treatment, said musical treatment for said appropriate complex cell replacement by said appropriate simple cell of said brain, and wherein said at least one or said combination of the treatments for said brain is provided to treat a complete said damage of said complex cell of said brain, and;
   providing said at least one or said combination of said visual treatment, said audio treatment, said kinesthetic treatment, said olfactory treatment, said tactual treatment, said musical treatment for a correction of an address of said appropriate complex cell by an assistance of said appropriate simple cell of said brain to process the submitted stimuli, and wherein said at least one or said combination of the treatments for said brain is provided to treat said partial damage of said complex cell of said brain.

2. The method of claim 1, wherein said either one of said visual treatment, said audio treatment, said kinesthetic treatment, said olfactory treatment, said tactual treatment and said musical treatment comprises the steps of:
   generalizing at least one or each of said pattern of said psychoconduction code providing a bank of said video information, said audio information, said kinesthetic information, said olfactory information, said tactual information and said musical information;
   selecting an arithmetical addition pattern from said pattern for learning of said arithmetical addition;
   selecting an arithmetical multiplication pattern from said pattern for learning of said arithmetical multiplication;
   selecting an arithmetical subtraction pattern from said pattern for learning of said arithmetical subtraction;
   selecting an arithmetical division pattern from said pattern for learning of said arithmetical division;
   selecting a reading pattern from said pattern for reading learning;
   selecting a writing pattern from said pattern for writing learning;

transforming said arithmetical addition pattern, said arithmetical multiplication pattern, said arithmetical subtraction pattern, said arithmetical division pattern, said reading pattern and said writing pattern by said psychoconduction code in either one of said audio pattern, video pattern, kinesthetic pattern, olfactory pattern, tactual pattern, musical pattern or their combination.

* * * * *